United States Patent
Larson

(10) Patent No.: US 9,592,022 B2
(45) Date of Patent: Mar. 14, 2017

(54) METHOD FOR CONSISTENT AND VERIFIABLE OPTIMIZATION OF COMPUTED TOMOGRAPHY (CT) RADIATION DOSE

(71) Applicant: Children's Hospital Medical Center, Cincinnati, OH (US)

(72) Inventor: David B. Larson, Los Altos, CA (US)

(73) Assignee: Children's Hospital Medical Center, Cincinnati, OH (US)

( * ) Notice: Subject to any disclaimer, the term of this patent is extended or adjusted under 35 U.S.C. 154(b) by 201 days.

(21) Appl. No.: 14/348,216

(22) PCT Filed: Oct. 1, 2012

(86) PCT No.: PCT/US2012/058310
§ 371 (c)(1),
(2) Date: Mar. 28, 2014

(87) PCT Pub. No.: WO2013/049818
PCT Pub. Date: Apr. 4, 2013

(65) Prior Publication Data
US 2014/0270053 A1    Sep. 18, 2014

Related U.S. Application Data

(60) Provisional application No. 61/541,671, filed on Sep. 30, 2011.

(51) Int. Cl.
*A61B 6/00* (2006.01)
*A61B 6/03* (2006.01)

(52) U.S. Cl.
CPC ............ *A61B 6/5258* (2013.01); *A61B 6/032* (2013.01); *A61B 6/405* (2013.01); *A61B 6/463* (2013.01);
(Continued)

(58) Field of Classification Search
CPC ..... A61B 6/032; A61B 6/5205; A61B 6/5258; G01N 2223/419; G01N 23/04; G01N 2223/401
See application file for complete search history.

(56) References Cited

U.S. PATENT DOCUMENTS

| 6,307,912 B1 | 10/2001 | He et al. |
| 8,891,849 B2 | 11/2014 | Rohler et al. |
| 2004/0136498 A1 | 7/2004 | Omernick et al. |
| 2004/0202277 A1 | 10/2004 | Okumura et al. |

(Continued)

FOREIGN PATENT DOCUMENTS

| CN | 1695557 | 11/2005 |
| CN | 101897595 | 12/2010 |

(Continued)

OTHER PUBLICATIONS

Menke, Jan, Comparison of Different Body Size Parameters for Individual Dose Adaptation in Body CT of Adults, Radiology, Aug. 2005, pp. 565-571, vol. 236, No. 2, Radiological Society of North America, Oak Brook, IL, USA.

(Continued)

*Primary Examiner* — Hoon Song
(74) *Attorney, Agent, or Firm* — Baker & Hostetler LLP

(57) ABSTRACT

A system and a method is disclosed for consistently and verifiably optimizing computed tomography (CT) radiation dose in the clinical setting. Mathematical models allow for estimation of patient size, image noise, size-specific radiation dose, and image quality targets based on digital image data and radiologists preferences. A prediction model estimates the scanner's tube current modulation and predicts image noise and size-specific radiation dose over a range of patient sizes. An optimization model calculates specific scanner settings needed to attain target image quality at the minimum radiation dose possible. An automated system processes the image and dose data according to the mathematical models and stores and displays the information, enabling verification and ongoing monitoring of consistent dose optimization.

59 Claims, 24 Drawing Sheets

(52) U.S. Cl.
CPC .............. *A61B 6/488* (2013.01); *A61B 6/544* (2013.01); *A61B 6/545* (2013.01); *A61B 6/583* (2013.01); *A61B 6/563* (2013.01); *F04C 2270/041* (2013.01)

(56) References Cited

U.S. PATENT DOCUMENTS

| | | |
|---|---|---|
| 2005/0058250 A1* | 3/2005 | Popescu ................ A61B 6/032 378/109 |
| 2007/0081630 A1 | 4/2007 | Evron |
| 2007/0258559 A1 | 11/2007 | Hur |
| 2008/0118032 A1 | 5/2008 | Graham et al. |
| 2009/0168950 A1 | 7/2009 | Jianying |

FOREIGN PATENT DOCUMENTS

| | | |
|---|---|---|
| DE | 102005004383 A1 | 8/2006 |
| DE | 102008014738 A1 | 9/2009 |
| WO | 2011008296 A1 | 1/2011 |

OTHER PUBLICATIONS

International Search Report and Written Opinion, from PCT/US2012/058310 with an international filing date of Oct. 1, 2012, mailed from the United States Receiving Office of the PCT on Feb. 8, 2013, 11 pages, Alexandria, Virginia,USA.
Size-Specific Dose Estimates (SSDE) in Pediatric and Adult Body CT Examinations, AAPM Report No. 204, ISBN-978-1-936366-08-8, ISSN: 0271-7344, American Association of Physicists in Medicine, pp. 1-26, 2011.

* cited by examiner

2400

Query Studies

| MRN: | | Patient Age Range: | From: | To: | Scanner(s) ▼ |
| Patient Name: | | Study Date Range: | | | Study Description ▼ |
| Accession Number: | | Processed Date Range: | | | Study Protocol ▼ |
| | | | | | Body Type ▼ |

Saved Queries
Owner: [ ▼ ]   Query Name: [ ▼ ]

[Display Charts]   [Search]   [Reset]   [Save Query]

| MRN | Name | Age | DOB | Accession | Study Date | Study Descript | Scanner Protocol |
|---|---|---|---|---|---|---|---|
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |
| ▶ 123456789 | Doe, John | 2 yr | 7/2/2009 | 123456789 | 7/5/2011 | CT ABDOMEN | CCMCT0 CT Abd Pel 0-15 kg |

FIG. 24

ROUTINE ABDOMEN AND PELVIS WITH CONTRAST

SCOUT

| | |
|---|---|
| PATIENT POSITION | Supine with arms elevated |
| LANDMARK | Nipple Line |
| kVp | Up to 46 kg 100 kVp |
| | >46 kg 120 kVp |
| mA (two scouts) | Up to 46 kg 30 mA |
| | >46 kg 50 mA |
| BREATH HOLD | Inspiration |

TECHNICAL FACTORS

| | |
|---|---|
| SCAN TYPE | Helical |
| kVp | Up to 46 kg - 100 kVp |
| | >46 kg 120 kVp |
| mA | ATCM |
| ROTATION TIME | 0.5 second |
| DETECTOR ROWS | 0.5 x 64 |
| PITCH | 0.828 (HP 53) |
| SLICE THICKNESS | Up to 15 kg 3.0 mm |
| | >15 kg 5.0 mm |

CONTRAST

| | |
|---|---|
| ORAL CONTRAST | Omnipaque |
| ORAL CONTRAST VOL | See chart |
| I.V. CONTRAST | Optiray 320 |
| I.V. CONTRAST VOL | 2 mL/kg up to 100 mL max |
| PREF I.V. GAUGE | 22g or larger |
| PREF I.V. LOCATION | n/a |
| FLOW RATE | 2 mL/sec |

This imaging exam requires contrast and/or medications to be administered through an intravenous (IV) catheter. If a peripheral IV catheter is in place and is determined to be functioning properly it is to be used for this purpose. If a central venous catheter is in place, it can be used in accordance with the existing departmental guideline. If there is no working intravenous catheter in place, this exam requires one to be placed, according to departmental guidelines. If a catheter is placed, it is to be removed at the conclusion of the exam, unless there is a specific request by anesthesiology, radiology, or other service or healthcare provider to maintain the catheter beyond that time.

SCAN

| | |
|---|---|
| START/END LOCATION | Lung bases through pubic symph |
| SHIELDING | Breast Shield |
| BREATH HOLD | Inspiration |
| SCAN DELAY | 30 sec after HU trigger |
| REMINDERS | For Crohn's, extend imaging below perineum |

RECONSTRUCTIONS

| | |
|---|---|
| ABD/PEL STD AXIAL | FC 12 (QDS+) 5.0 mm <15 kg 3.0 mm |
| ABD/PEL STD VOL | FC 12 (QDS+) 0.5 x 0.3 mm |
| CORONAL MPR | FC 12 (QDS+) 3.0 mm posterior to anterior |

FIG. 29

METHOD FOR CONSISTENT AND VERIFIABLE OPTIMIZATION OF COMPUTED TOMOGRAPHY (CT) RADIATION DOSE

CROSS-REFERENCE TO RELATED APPLICATIONS

The present application is a national stage entry of PCT/US2012/058310, filed Oct. 1, 2012, which claims the benefit of U.S. Application Ser. No. 61/541,671, filed Sep. 30, 2011.

FIELD OF THE INVENTION

The current disclosure relates to a Computed Tomography (CT) method for optimizing radiation dose. The current disclosure also relates to an integrated system to provide consistent CT radiation dose optimization based on individual patients throughout an organization by minimizing deviation from quantitative image quality targets.

BACKGROUND OF THE INVENTION

Hospitals are beginning to monitor CT radiation dose in response to issued health guidelines. When undergoing medical radiation exposure, including that of computed tomography (CT), the guiding principle is that of As Low As Reasonably Achievable (ALARA). Thus, imagers desire to use the minimum radiation dose necessary to achieve diagnostic image quality. Radiation doses that are too low produce images of inadequate quality. Radiation doses that are too high place the patient at risk without added diagnostic quality. Therefore, the problem of ALARA in CT may be viewed as an image quality optimization problem in addition to a radiation dose optimization problem. Specifically, imagers' ability to optimize dose depends on their ability to accurately predict image quality prior to the CT examination and prospectively use radiation dose parameters that will result in image quality that is just above the diagnostic threshold.

All else being equal, higher radiation dose in a CT scanner results in a clearer image. Two major factors under the direct control of the operator contribute to the radiation dose: the energy level of the beam, measured as the tube voltage (kV), and the fluence of photons, measured as a function of the tube current and time (mAs). Radiation dose delivered to the patient is proportional to the fluence and approximately proportional to the square of the tube current. Lowering the dose reduces the number of photons arriving at the detector and results in a grainier, or noisier, image. Higher dose levels are required to maintain image quality in larger patients and lower dose levels are required in smaller patients. The goal for the operator is to use the lowest radiation dose possible to generate images of diagnostic quality. To date, image quality measurements for clinical examinations are typically not available to radiologists.

The limiting image quality characteristic for low-contrast applications such as CT of the abdomen/pelvis tends to be that of low contrast detectability (LCD), which incorporates both spatial and contrast resolution estimates. The method of measuring image quality for the present disclosure is that of image noise, which can be used as a proxy for LCD as it provides a single image quality measure. CT parameters must be set prior to the examination; therefore, if parameters are to be based on a minimum image quality, the user must know a priori what parameters should be used that will result in the lowest radiation dose possible to generate images of diagnostic quality.

Several radiation reduction techniques, including dose modulation, are incorporated into most modern CT scanners. However, radiation dose remains under the control of the operator, who retains the ability to set scan parameters such as kV, mA, and acceptable "noise factor" parameters for dose modulated examinations. Yet radiologists are still currently limited in many respects, including the following:

a) Image quality is difficult to quantify, even by visual inspection; thus, standard image quality metrics have not been well established.
 b) Image quality depends on both scan parameters and patient size; a quantitative model of how these factors interact to impact image quality has not been well established.
 c) Even if it could be measured, without a predictive model, image quality can only be assessed after the scan has been completed, limiting its usefulness.
 d) Minimum image quality thresholds have not been established.

Furthermore, CT utilization has substantially increased in recent years. Many scanners perform dozens of examinations per day, operated by CT technologists, supervised by radiologists, with the aid of physicists, none of whom are currently reimbursed for optimizing image quality or radiation dose. It would be unreasonable to expect that these individuals would dedicate a large amount of their time to ensure image quality/dose optimization. Thus, even if a method of quantifying image quality is developed, unless it is integrated into the current workflow with minimal disruption and is easy to use, it is unlikely to experience widespread adoption.

Many of the current challenges surrounding CT dose optimization are related to the problem of image quality and dose verification. Without an automated system, radiologists who believe or claim that they optimize dose can only verify this at great expense, if at all, due to the difficulty in acquiring, analyzing, aggregating, and reporting data from individual scans.

Thus, while quantitative image quality assessment is an important element, the system must also be practical. Specifically, the system should satisfy several principles:

1. Prediction: The system should predict image quality based on scan parameters and patient size.
 2. Optimization: The system should recommend scan parameters that are expected to produce images of desired quality at the lowest possible dose (ALARA).
 3. Assessment: The system should assess how well an individual scan achieves the goal of ALARA relative to other scans.
 4. Monitoring: The system should enable a manager to ensure that ALARA is consistently achieved on all studies on all scanners in an organization.
 5. Verification/reporting: The system should enable an enterprise to report its performance in a quantifiable way.
 6. Automation/integration: To the extent possible, the system should function automatically, requiring minimal manual data input.
 7. Transparency: At the same time, the system should be as transparent as possible, informing operators and managers of both individual and aggregated study performance.

8. Controllable: While the system should function automatically, it should also allow overriding operator control at any time.
9. Ease of use: The system should be intuitive and as simple to use as possible.

SUMMARY OF THE INVENTION

The exemplary embodiments provide a system or method which utilizes quantitative image quality assessments and radiation dose estimates to achieve radiation dose levels that are As Low As Reasonably Achievable (ALARA) on a consistent basis for Computerized Tomography (CT) scanners in an organization.

In an embodiment, a method for generating scan parameters for a CT scanner is disclosed. The method first obtains patient size data. Next, the method establishes an image quality preference profile for a single radiologist or group of radiologist, the image quality preference profile being a function of image quality and patient size data. Next, the method establishes a target noise equation, derived from the image quality preference profile. Next, the target noise equation is applied against a measured noise equation, the measured noise equation being a function of the patient size data, to derive scan parameters for a given scan. In a more detailed embodiment, the step of applying the target noise equation against a measured noise equation to derive scan parameters for a given scan may include a step of setting the target noise equation equal to measured noise equation for the patent size data, and solving for a radiation dose parameter. In a further detailed embodiment, the radiation dose parameter may include mAs, given other scanner parameters. In a further detailed embodiment, the image quality preference profile equation may be:

$$S = 1 + \frac{4}{\left[1 + Ae^{(B\sigma \cdot e^{-CD_W})}\right]}$$

where S is the image quality preference score, $D_W$ is patient size data, and A, B, and C are empirically-derived constants. In a further detailed embodiment, the target noise equation is derived from the image quality preference profile equation and may be $$\sigma_T = c_T + a_T \cdot e^{bT} \cdot e^{bT \cdot D_W}$$

where $\sigma_T$ is the target noise, $c_T$, $a_T$, and $b_T$ are empirically-derived constants and where $D_W$ is patent size data, which is water-equivalent diameter for the patient. And in a further detailed embodiment, the measured noise equation may be $$\sigma = c_0 + c_1 (c_{m_e} m_e)^{c_2} e^{[D_W c_3 (c_{m_e} m_e)^{c_4}]}$$

where $c_0$, $c_1$, $c_2$, $c_3$, $c_4$, and $c_{me}$ are empirically-derived constants and $m_e$ is effective mAs. The step of solving for the radiation dose parameter may be an iterative process. The image quality preference profile equation may be established, at least in part, upon one or more radiologist's subjective assessments of appropriate image quality.

Alternatively, or in addition, the patient size data may be a water-equivalent diameter, $D_W$, of the patient. Alternatively, or in addition, the measured noise equation may be derived from noise measurement data taken from a conical water phantom. Alternatively, or in addition, the image quality preference profile equation may be used to derive a target noise equation that maintains a constant image quality preference score over a range of patient sizes. Alternatively, or in addition, the image quality preference score is selected based on desired image quality for a specific CT application; such as, for example, a body target application, a lung target application and/or a bone target application. Alternatively, or in addition, the patent size data may be a mean value of water-equivalent diameter taken for a patient over a scan axis, and the mean value of water-equivalent diameter may be derived by, for example, performing a row-by-row integration of tomogram image data for each cross-sectional level along the scan axis. Alternatively, or in addition, the scan parameters may include scan mode, kV, mA and/or dose modulation settings, rotation speed, pitch, bowtie filter, and/or focal spot size. Alternatively, or in addition, the method further includes a step of performing image data and metadata from a CT scan utilizing one or more of the derived scan parameters. Alternatively, or in addition, the method may further include a step of storing the derived scan parameters and the patient size data in a database record associated with the CT scan for subsequent data analysis. Alternatively, or in addition, the method may further include a step of displaying the scan data, including slice-by-slice patient size data, effective mAs data, and derived image noise data superimposed upon the topogram image. Alternatively, or in addition, the method may further include a step of signalling if one or more of the derived scan parameters fall outside of a set of selected scan parameters.

In another embodiment, a method for determining a size specific radiation dose estimate (SSDE) for a patient in a computed tomography (CT) scan, using a scanner, includes the following steps: estimating a patient water equivalent diameter ($D_W$); establishing a target image quality parameter for the scan at least partially based on $D_W$; retrieving scanner parameters from a database; determining the SSDE based on the target image quality parameters, and the scanner parameters; recommending the SSDE; scanning the patient utilizing a radiation dose, based, at least in part, upon the recommended SSDE; displaying the scan image; measuring the scan image for noise information; and updating the database. In a more detailed embodiment, the method may further include processing water phantom images to yield scanner parameters by scanning a water phantom and saving an image noise information and scanner parameters a database. Alternatively, or in addition, the step of scanning the patient may include administering the determined SSDE. Alternatively, or in addition, the step of estimating $D_W$ may include scanning a patient with a scout scan, and creating a topogram with the scout scan.

Alternatively, or in addition, the method may further include: performing a row-by-row integration of the topogram by the scanner to determine water equivalent diameter for a slice ($D_{W\_net}$) for each cross-sectional level along the z-axis; and mapping $D_{W\_net}$ to the topogram. In addition, the method may further include calculating the estimated noise calculated at each slice and mapping the estimated noise to a topogram.

Alternatively, or in addition, the step of estimating the patent size $D_W$ may be accomplished by: scanning the patient with a scout scan to acquire the patient's thickness $T_W$; and using $T_W$ to cross-reference corresponding $D_W$ from the database.

Alternatively, or in addition, the step of updating the database may include aggregating the parameters in the database with the SSDE information, the noise information, the scanner parameters, and/or $D_W$.

Alternatively, or in addition, the scanner parameters may include scanner constants and scanner performance data. Further, the method may include steps of deriving scanner parameters by performing at least one water phantom scan, with at least one scanner setting and mode; measuring the noise; solving for a chosen constant with an appropriate equation; and saving the settings parameters and image noise to the database. Further, the scanner characteristics may be derived by scanning the water phantom and measuring the noise values, where the water phantom may be on a table or off a table. The water phantom may be a conical object filled with water, having a diameter range of about 5 cm to 40 cm.

Alternatively, or in addition, the scanner parameters may include, for at least one mode and one setting: $c_{scout}$; magnification factor (m.f.); target noise constants $c_T$, $a_T$, and $b_T$; noise constants $c_0$, $c_c$, $r_c$, $c_r$, $r_r$, and $c_{em}$; a, b; contrast sensitivity; and special resolution; and/or a dose kV, mA, mAs; a dose $CTDI_{vol}$; dose length product (DLP). The method may further include steps of: deriving $c_{scout}$ for the scanner by scanning the water phantom with a known thickness $T_W$; solving for $c_{scout}$ where $T_W = c_{scout} DU$, where DU is density units, and saving $c_{scout}$ to the database; and using the constant $c_{scout}$ to determine $D_W$, where $$D_W = 2 \cdot c_{scout} \sqrt{\frac{DU_{sum}}{\pi}}.$$

Alternatively, or in addition, $c_T$, $a_T$, and $b_T$ may be derived by: scanning a water phantom with diameter $D_W$; measuring the noise from the water phantom scan; solving for the equation $$\text{Target noise} = c_T + a_T e^{b_T \cdot D_W}$$

and transmitting the values of $c_T$, $a_T$, and $b_T$ to the database. Alternatively, or in addition, constants $c_0$, $c_c$, $r_c$, $c_r$, $r_r$, and $c_{em}$ may be derived by: scanning a water phantom having diameter $D_W$; measuring the noise from the water phantom scan; solving for the equation $$\text{Noise} = c_0 + c_c (c_{SD} \cdot SD)^{r_c} \cdot e^{[c_r (c_{SD} \cdot SD)^{r_r} \cdot D_W]}$$

and transmitting the values of $c_0$, $c_c$, $r_c$, $c_r$, $r_r$, and $c_{em}$ to the database.

Alternatively, or in addition, the method may further include providing a display output to graphically show a measure of CT image quality for the scan. Alternatively, or in addition, the target image quality parameter may be based on a target visual noise parameter. The step of establishing a target visual noise parameter for a CT scan may include a step of determining the point where a dose modulation noise curve is equal to a target noise curve. The dose modulation noise curve may be modeled according to the following equation:

$$\text{Noise} = c_0 + c_c (c_{SD} \cdot SD)^{r_c} \cdot e^{[c_r (c_{SD} \cdot SD)^{r_r} \cdot D_W]}$$

and the constants $c_0$, $c_c$, $r_c$, $c_r$, $r_r$, and $c_{em}$ are aggregated scanner parameters in the database, and wherein SD a variable target noise scanner setting. The target image noise curve may be established according to the equation:

$$\text{Target noise} = c_T + a_T e^{b_T \cdot D_W}$$

wherein $c_T$, $a_T$, and $b_T$ are scanner parameter constants found in the database. The method may further include recommending scan parameters to an operator according to the target image curve.

Alternatively, or in addition, the step of determining the SSDE, may include using $D_W$ and solving for the equation: $SSDE = (a \cdot e^{-b \cdot D_W}) CTDI_{vol}$. The method may further including calculating a dose-length product (DLP), where the DLP is the product of the $CTDI_{vol}$ and the length of the scan, based on the calculated $CTDI_{vol}$ for each slice n, and saving the DLP to the database.

Alternatively, or in addition, the method may further include: (i) calculating statistics for a study including the minimum, mean, and maximum for one or more of the following parameters: a flow of photons in the dose (mA), the water equivalent diameter ($D_W$), water equivalent diameter for a slice ($D_{W\_net}$), an estimation of radiation dose ($CTDI_{vol}$), a dose length product, the product of the $CTDI_{vol}$ and the length of the scan (DLP), SSDE, and noise; (ii) transmitting one or more of the parameters to the database; and (iii) retrieving data from the DICOM header information, including patient name, accession number, medical record number, date of birth, date of the examination, scanner, medical center, and/or examination name.

Alternatively, or in addition, the method may further include: receiving an operator input to a range of acceptable image quality parameters; incorporating $D_W$ and scanner parameters to calculate a SSDE for the range of acceptable image quality values; recommending the SSDE that would generate images with acceptable image quality parameters; allowing an operator to manually set the SSDE; and displaying an output on whether the expected image quality falls within the acceptable image quality parameters. The method may further include receiving input for a target image quality parameter; calculating a study with the input image quality parameter; and recommending specific scan parameters, including at least one of: kV, mA, and dose modulation settings to achieve the input image quality. Alternatively, or in addition, the method may include: providing an alert when SSDE is higher or lower than the recommended SSDE; and providing an alert if the expected image quality falls outside the acceptable image quality parameters. Alternatively, or in addition, the method may include displaying in a chart scans that fell within expected image quality parameters versus scans that fell outside expected image quality parameters.

Alternatively, or in addition, the method may further include: maintaining scan protocols for a plurality of scanners within a central database; and interfacing with a central protocol manager with a plurality of scanners to update protocol changes for the plurality of scanners.

Alternatively, or in addition, the method may include recommending a protocol to a patient of size Dw based on previously acquired data.

Another embodiment is directed to a system capable of performing the methods summarized above, for minimizing radiation dose while achieving image quality comprising in CT scanning. Such a system may include a protocol manager including a processor; a study performance database in communication with a scanner, the database including scanner parameters; the scanner capable of scout scanning and CT tomography scanning; a dose registry; and a protocol database.

A disclosed method processes water phantom images to yield data relating water-equivalent diameter to image noise. Visual noise may be measured from a water phantom because water is known to be homogenous in density, and the diameter is measurable, and can be varied. Using these water phantoms, noise can be charted to diameter. The system or method may automatically processes water phantom images to yield data relating water-equivalent diameter to image noise. Visual noise can be measured from a water phantom because water is known to be homogenous in density, and the diameter is measurable, and can be varied. Using these water phantoms, noise can be charted to diameter.

The method may establish a target image quality using a radiologist's perception of adequacy of image quality compared to patient water equivalent diameter and image noise. Radiologists can tolerate different levels of noise for patients of different sizes, as well as different parts of the body. Generally, the larger the patient, the greater the noise lever a radiologist can tolerate. The system can establish a target image quality using a standard radiologist's perception of adequacy of image quality compared to patient water equivalent diameter and image noise. Generally, radiologists can tolerate different levels of noise for patients of different sizes, as well as different parts of the body. This is known to practicing radiologists, and CT manufacturers. A mathematical model may be for predicting image noise based on water equivalent diameter and effective mAs at all scan modes and settings. Using the measured water phantom noise from experiments, a mathematical model may be obtained: Noise=$c_0+c_c(c_{em} \cdot em)^{r_c} \cdot e^{[c_r(c_{em} \cdot em)^{r_r} \cdot D_W]}$. This mathematical model may be used in CT scans to predict noise. Alternatively, a mathematical model for predicting image noise based on water equivalent diameter and dose modulation settings at all scan modes and settings may be described as:

$$\text{Noise} = c_0 + c_c(c_{SD} \cdot SD)^{r_c} \cdot e^{[c_r(c_{SD} \cdot SD)^{r_r} \cdot D_W]}$$

The method may process the topogram image to quantitatively measure patient size at each z-axis level, and may use a processor to perform a row-by-row integration of the topogram to determine $D_{W\_net}$ for each cross-sectional level along the z-axis, and may use the DICOM header and map it to the topogram.

The system may incorporate patient size characteristics, known scanner performance data, and scan parameters to provide a measure of CT image quality for each image for all scan modes and settings. The estimated noise may be calculated at each slice and mapped to the topogram. The estimated noise may be calculated at each slice and mapped to the topogram.

The system may process the topogram image to quantitatively measure patient size at each z-axis level. The processor may perform a row-by-row integration of the topogram to determine $D_{W\_net}$ for each cross-sectional level along the z-axis, and may use the DICOM header and map it to the topogram.

The dose modulation parameters may produce a formula to be set to the Target Noise curve to obtain the optimal target noise. The system may modulate dose based on patient size. A mathematical model may be provided for optimizing radiation dose settings by determining tube current, dose modulation settings, and other settings need to match predicted image noise with target image noise. The target noise may be found by setting Target noise=$c_T$+ $a_T \cdot e^{b_T \cdot D_W}$ to Noise=$c_0+c_c(c_{SD} \cdot SD)^{r_c} \cdot e^{[c_r(c_{SD} \cdot SD)^{r_r} \cdot D_W]}$ to optimize the dose (find the point they cross). Curves may be modeled using these equations, and using these curves, work backwards to give the settings to be set at: when Noise=target noise. EmAs—solve iteratively.

In another embodiment, a system is disclosed. The system incorporates the method of optimizing a scan above, and integrates it into a comprehensive system. The system processes the data acquired by the scanner, and then provides feedback to the scanner. The system that aggregates the measures of image quality based on patient size characteristics of a multiple scans to assess how image quality compares to other scans. A study analysis page collects and displays information and charts, and compares studies to plot all in one graph. The system models a target image curve, and displays aggregate data with plots against the collected data.

Prior to a scan, the system may incorporate patient size characteristics and acquired scanner performance data to recommend specific scan parameters, including kV, mA, and dose modulation settings, to achieve a study with a desired image quality. The system provides information on whether the expected image quality falls within desired parameters.

The system may recommend scan parameters or provide alerts when radiation dose is higher or lower than recommended predicted dose. The system may recommend scan parameters that would generate images with expected image quality values that fall within desired parameters given patient size characteristics.

Following one or more scans, the system may display which scans fell within expected image quality parameters, and which ones fell outside expected image quality parameters. The system may calculate, chart, and display analysis pages and include plots, and reports in a graphical representation.

The system may provide an alert when the variation of image quality of aggregated scans has changed or has begun to fall outside desired parameters.

The system may centrally maintain all scan protocols for all scanners in an enterprise within a single database, with the capability of interfacing with all scanners in a given organization to update protocol changes for all scanners. The system may also report within the organization, or outside an organization, for example, if hospitals are one day required to report this to a regulatory agency.

The system may report expected image quality measures over a range of patient sizes for each scan protocol, and pull together various scans or scan studies to display quality and other parameters and statistics for a range of patient sizes. The system can recommend a protocol depending on patient size.

The system may report, in electronic or print format, measures of image quality and dose related to scans performed within the organization. System that can report, in electronic or print format, expected image quality measures of scan protocols to an individual or organization, internal or external to the organization.

The system may aggregate the measures of image quality based on patient size characteristics of multiple scans to assess how image quality compares to other scans. FIG. 31 shows a study analysis page which collects and displays information and charts plotted to in one graph.

The system may compare aggregate measures of image quality based on patient size characteristics to a target image quality curve, which also incorporates patient size characteristics.

The system may prospectively incorporate patient size characteristics and known scanner performance data to recommend specific scan parameters, including kV, mA, and dose modulation settings, to achieve a study with a desired image quality. Once the target image curve is established and the system runs the calculations, the system may recommend scan parameters to the CT technologist. These steps are taken to find the proper dose for a patient.

The system, based on patient size characteristics and scan parameters, may prospectively informs the operator whether the expected image quality falls within desired parameters. The system may recommend scan parameters to the CT technologist, or provides alerts when radiation dose is higher or lower than recommended dose.

The system may prospectively recommend scan parameters that would generate images with expected image quality values that fall within desired parameters given patient size characteristics. The system may recommend scan parameters to the CT.

The system, based on patient size characteristics and scan parameters, may prospectively alert the operator if expected image quality falls outside desired parameters. All parameters can control target noise parameter (SD) setting (Max, Min, SD, Automated). The system may recommend the dose parameter settings.

The system may illustrate, retrospectively, which scans fell within expected image quality parameters versus which fell outside expected image quality parameters, based on patient size. The system can also pull together analysis pages and include plots, and reports.

The system may calculate the parameters that should have been used on scans with image quality that fall outside desired parameters in order to have achieved a scan with image quality that falls within desired parameters. A database application can analyze the scans afterwards and inform the operator what the operator did, and what the operator should have done.

The system may alert the user if/when the variation of image quality of aggregated scans has changed or has begun to fall outside desired parameters. The application may organize this information of scan quality in a chart, to be less daunting, and more transparent, as shown in FIG. 33.

The system may maintains all scan protocols for all scanners for a given enterprise within a single database, with the capability of interfacing with all scanners in a given organization to update protocol changes for all scanners. A single central database and protocol manager may used be for an organization, that all scanners in that organization can access, instead of protocols in each scanner. Individual institutions may set their own standards.

The system may prospectively illustrate expected image quality measures over a range of patient sizes for each scan protocol. The application can pull together these studies to show how different patient sizes compare. Based on protocol, the system can recommend a protocol depending on patient size.

The system can report, in electronic or print format, measures of image quality and dose related to scans performed within the organization. The system can interface within one organization and database, and report within the organization.

The system can report, in electronic or print format, expected image quality measures of scan protocols to an individual or organization, internal or external to the organization. The system can report outside an organization, for example, if hospitals are one day required to report this to a regulatory agency. The system may perform the above actions, including image processing, data storage, analysis, and monitoring in an automated fashion, for minimal disruption in the work flow.

BRIEF DESCRIPTION OF THE DRAWINGS

The present invention will be more apparent from the accompanying drawings, which are given by way of illustration only, and not to be limitative of the present invention. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 24 shows a screen shot of an example interface of a collection of studies;

DETAILED DESCRIPTION OF THE PREFERRED EMBODIMENTS

The system provides quantitative image quality assessment to achieve As Low As Reasonably Achievable (ALARA) on a consistent basis for all CT scanners in an organization. The system in the embodiments described below allows Computed Tomography (CT) scanners to incorporate scanner parameters and patient size into calculations to accurately determine the minimum radiation dose necessary to achieve diagnostic image quality. Finally, the embodiments below provide a comprehensive, transparent system to automate, analyze, and monitor the aggregate history of CT scans to ensure proper dosing and image quality across an organization.

Estimation Models

Figure 1:
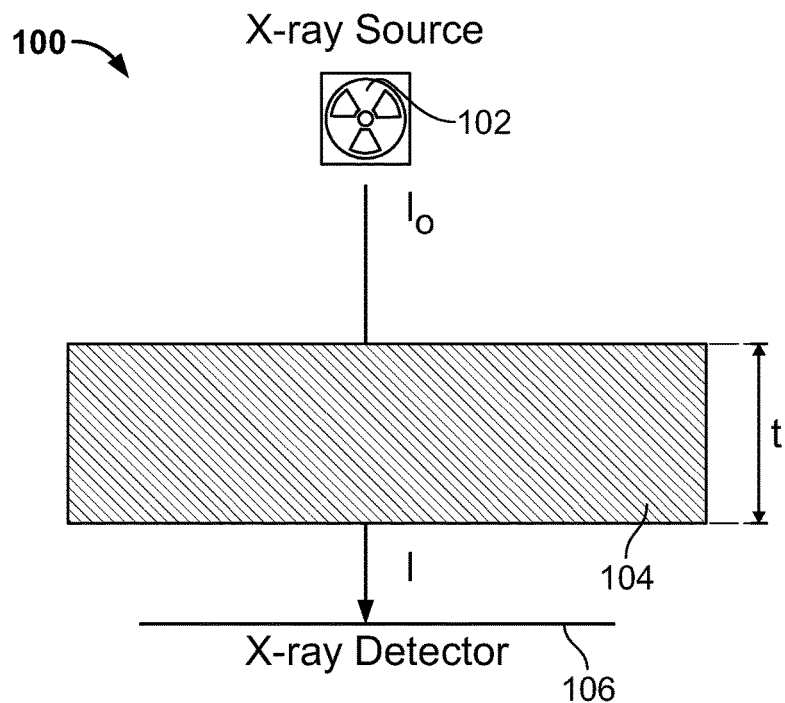
FIG. 1 depicts the basic schematic of a Computed Tomography device having an X-ray source.

FIG. 1 depicts the basic schematic of a CT device 100 having an X-ray source 102, and an X-ray detector 106 where $I_0$ is the initial intensity of the X-ray source, I is the Intensity at the X-ray detector after passing through t, a thickness of an object 104; The Beer-Lambert law describes attenuation characteristics of an x-ray beam with intensity $I_0$ as it travels through a medium 104 of thickness t:

$$I = I_0 e^{-\alpha t}$$

where I is the intensity of the x-ray beam after it passes through the medium 104 and $\alpha$ is the linear attenuation coefficient of the medium. Therefore attenuation of the beam, $I/I_0$, is a function of the thickness of the material and attenuation density of the material, which, in CT, is measured in Hounsfield Units. The image quality is a function of the intensity of the beam as it strikes the detector 106.

Patients are not of equal thickness or density. Therefore, if the intensity of the x-ray source is not appropriately adjusted, the dose will be higher than necessary; the source intensity must be adapted for the unique attenuation characteristics of the patient. Attenuation is a function of both patient thickness and tissue density, rotated around the patient. The half value thickness of water is approximately 3.4 cm at 60 keV, the typical beam energy corresponding to clinical CT. In other words, the source intensity, $I_0$, must double every 3.4 cm in order for I to remain constant. Thus, even relatively small differences in patient size result in large differences in dose necessary to maintain constant image quality. For this reason, appropriateness of dose must be expressed in terms of patient size.

Patient Size Estimation

Figure 2:
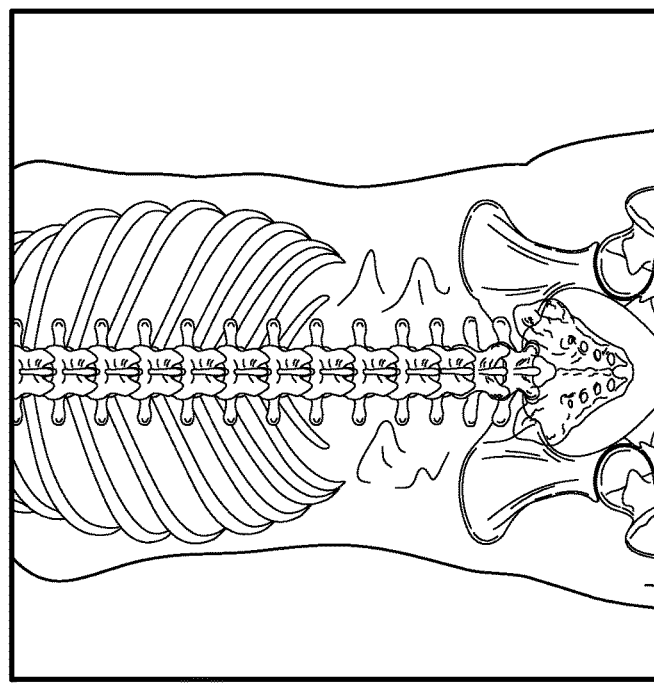
FIG. 2 shows an example topogram.

FIG. 2 shows an example topogram 200. For the purposes of CT, patient size can be measured as a single unit according to the water-equivalent diameter ($D_W$), which is estimated as a function of the average CT density of the tissues and the cross-sectional area of the patient. $D_W$ is the diameter of a cylinder of water that has the same average x-ray attenuation as a scanned body region 202.

$D_W$ can be estimated from the study topogram 200 of FIG. 2 performed by a scout, as described by Menke (Menke J. Comparison of different body size parameters for individual dose adaptation in body CT of adults. Radiology. 2005 August; 236(2):565-71. PubMed PMID: 16040914.) The topogram image 200 is based on a matrix of discrete data, which can be treated as density units (DU), with a higher value representing increased attenuation of the x-ray beam. These units are predictive of the water-equivalent thickness ($T_W$) of the material at that point. For example, for the Toshiba Aquilion scanner, the relationship is linear, and can be modeled according to the following equation:

$$T_W = c_{scout} DU$$

A row-by-row integral of the DU multiplied by the linear width of the scout yields a summation of density units multiplied by distance for each row ($DU_{sum}$). The constant $c_{scout}$ can be derived using the topogram from a CT study of a conical water phantom. The $DU_{sum}$ at each level can be plotted against the known diameter at each level to produce an equation correlating the $DU_{sum}$ with the $D_W$, according to the following equation:

$$D_W = 2 c_{scout} \sqrt{\frac{DU_{sum}}{\pi}}$$

Figure 3:
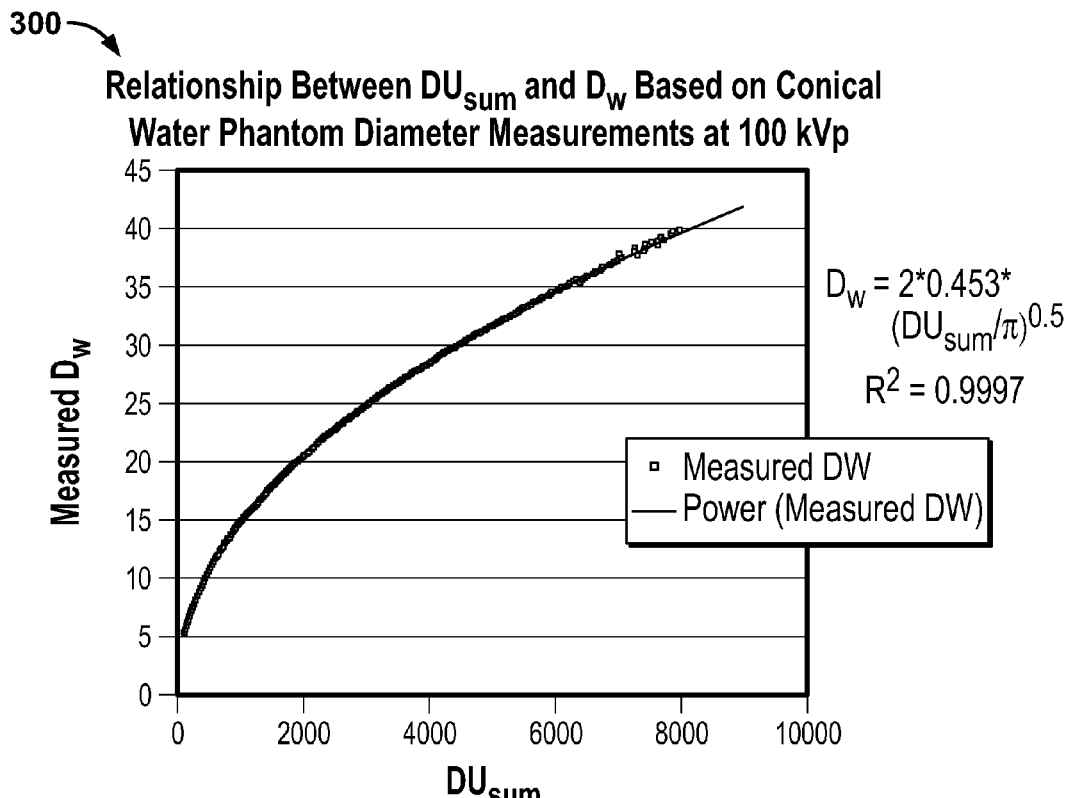
FIG. 3 is a chart of the power relationship between $DU_{sum}$ (Density Units) and $D_W$ (water diameter) for a conical water phantom diameter measured at 100 kV.

An example of the relationship between $DU_{sum}$ and $D_W$ based on a conical water phantom is shown in FIG. 3. FIG. 3 shows the power relationship 300 between $DU_{sum}$ (Density Units) and $D_W$ (water diameter) based on a conical water phantom diameter measured at 100 kV. The $c_{scout}$ is dependent on the kV, thus $c_{scout}$ must be calculated for each kV. However, $c_{scout}$ may be independent of the mA used on the topogram, as is the case for the Toshiba Aquilion.

Figure 4:
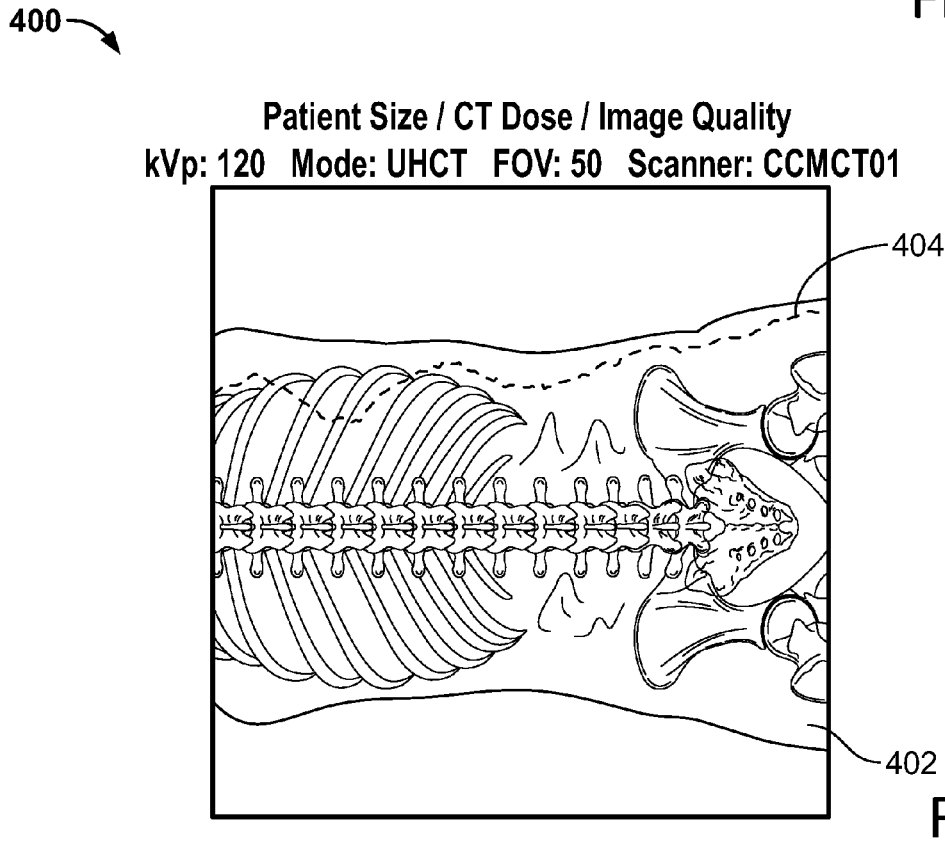
FIG. 4 shows $D_W$ calculated at each level, projected onto the topogram.

FIG. 4 shows $D_W$ calculated at each level, projected onto the topogram 400. As the cross-sectional diameter of the human body 402 varies along the z-axis, so does the $D_W$. The topogram data, $D_W$ is calculated at each level, and then projected onto the topogram image 404. The mean $D_{W\_mean}$ is calculated as a arithmetic mean of all of the $D_W$ values in the image. A weighted mean ($D_{W\_mean\_wt}$) may be calculated according to the following equation:

$$D_{W\_mean\_wt} = \sqrt{\frac{\sum_{1}^{n} D_W^2}{n}}$$

where n is the number rows used to calculate $D_{W\_wt}$.

Figure 5:
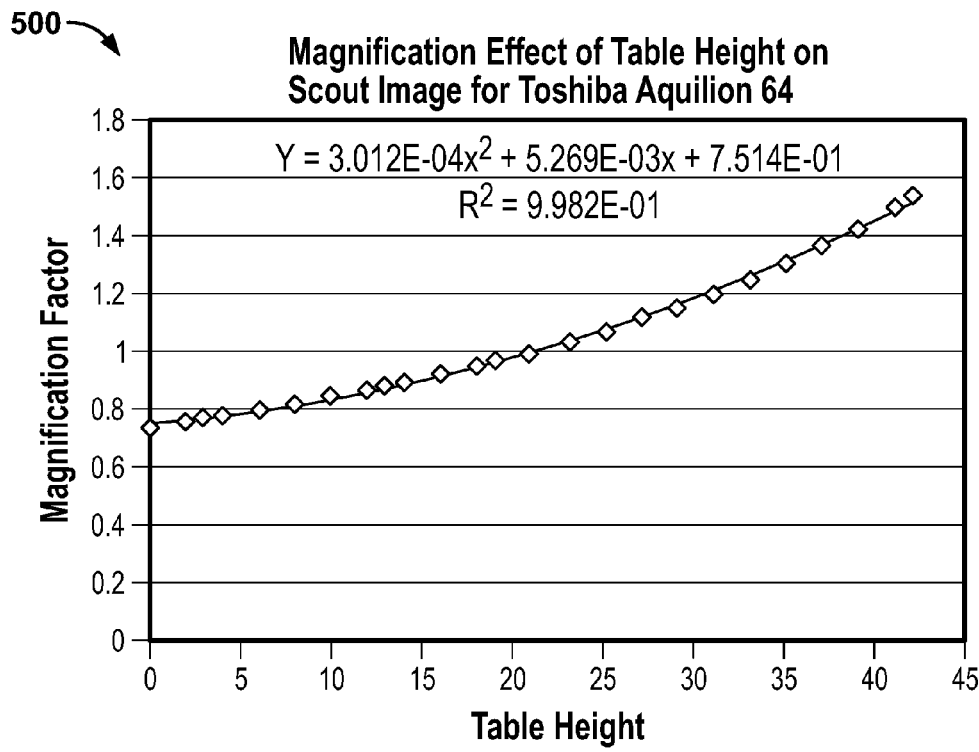
FIG. 5 is a graph showing the relationship between table height $h_t$ and magnification factor m.f.

FIG. 5 is a graph showing the relationship 500 between table height $h_t$ and magnification factor m.f. For a scan that includes the CT table (ie the CT couch), the anterior-posterior (AP) topogram data reflect x-ray attenuation by the table as well as by the patient. The table attenuation is subtracted from $DU_{sum}$ to yield the net density units ($DU_{sum\_net}$), which is then used to calculate the patient's water-equivalent diameter excluding the table, or $DU_{W\_net}$. However, the table is subject to magnification effects, depending on its vertical position. The relationship between the vertical height of the table ($h_t$) and the magnification factor (m.f.) is determined empirically, and can be expressed as the following equation:

$$m.f. = a h_t^2 + b h_t + c$$

where a, b, and c are empirically-derived constants for each scanner and the m.f. is:

$$w_{table\_actual} = m.f. \cdot w_{table\_proj}$$

$w_{table\_actual}$ is the actual table width and $w_{table\_proj}$ is the projected table width. The density units from the attenuation of the empty table ($DU_{table}$) is empirically measured for each kV. The sum of the attenuation units ($DU_{sum\_table}$) is calculated as $$DU_{sum\_table} = w_{table\_proj} \cdot DU_{table}$$

$DU_{sum\_table}$ is subtracted from $DU_{sum}$ to yield $DU_{sum\_net}$.

For a scan that includes only a lateral topogram, which primarily occurs in head CTs, the water-equivalent diameter does not subtract out the attenuation due to the head-holder, since head-holders are not of uniform size or shape and are not subject to magnification effects to the same extent as the table. Therefore, the attenuation data due to the holder cannot be reliably subtracted from the image.

To obtain patient size, $Dw_{net}$, from the topogram, first the total density units (DU) of the table is found, accounting for magnification:

$$T_{w\_proj} = \frac{T_{w\_actual}}{mf}$$

where $T_{w\_proj}$ is projected table width, $T_{w\_actual}$ is actual measured table width, and mf is the magnification factor.

$$mf = a \cdot T_h^2 + b \cdot T_h + c$$

where $T_h$ is table height (as measured/reported on scanner/in dicom) and a, b, and c are constants.

$$DU_{table\_sum} = T_{w\_proj} \cdot T_{dn}$$

where:
$DU_{table\_sum}$ is the sum of density units represented by the table,
$T_{w\_proj}$ is the projected table height and
$T_{dn}$ is the average density of the empty table
Note: If $Tw_{proj} > ScFOV$ (where ScFOV is Scout Field of view, or width), then $Tw_{proj} = ScFOV$ $$DU_{sum\_net} = DU_{sum} - DU_{table\_sum}$$

where
$DU_{sum\_net}$ is the sum of the scout density units with table subtracted and $DU_{sum}$ is the sum of the density units of the scout.

$$Dw_{net} = 2 \, c_{scout} \sqrt{\frac{DU_{sum\_net}}{\pi}}$$

where $Dw_{net}$ is the average size of the patient in Dw (cm), and $c_{scout}$ is a scout constant, unique for different kV values, but is constant for different mA values for the Toshiba Aquilion scanner.

The above calculations are performed on studies where an AP topogram is reliably performed and the table is reliably included, such as for CT of the chest, abdomen, and pelvis. For head and neck CT, which often only include a lateral topogram view, the table is not subtracted out. Also note, that if the table is subtracted out, the noise model that was developed with the phantom on the table must be used. If the non-subtracted Dw is used, the noise model must be used that was developed with the phantom off the end of the table. See sheets Ag1_Mod_Const_AP and Ag1_mod_Const_Lat for constants and for examples, on file "Guidance app prototype" or "CCMCT01 Model Constants 20110727." For dose calculations, see sheet Dose_Calculations on same file. SSDE was calculated using AAPM Report No. 204, "SSDE in Pediatric and Adult Body CT Examinations."

Conversion from $CTDI_{32}$ to $CTDI_{16}$ depends on Dw using constants derived from setting equation A-1 for 16 cm and 32 cm phantoms See Ag1_Dose_Calculations sheet for equations and examples.

Image Noise and Radiation Dose Estimation

Several elements contribute to the diagnostic quality of an image, including contrast sensitivity, spatial resolution, visual noise, blurring/visibility of detail, and artifacts. For the most part, artifacts and blurring/visibility of detail reflect scanner design and patient characteristics and generally are not directly related to the dose settings for the scan. Elements that are directly affected by the radiation dose of the scan include contrast sensitivity, spatial resolution, and visual noise. These factors are incorporated into delectability, which is perhaps the primary consideration in determining CT image quality. Low-contrast delectability (LCD) dominates image quality where contrast differences between tissues are small, such as for CT of the abdomen and pelvis, which also are the examinations which use the highest effective radiation doses.

Figure 6:
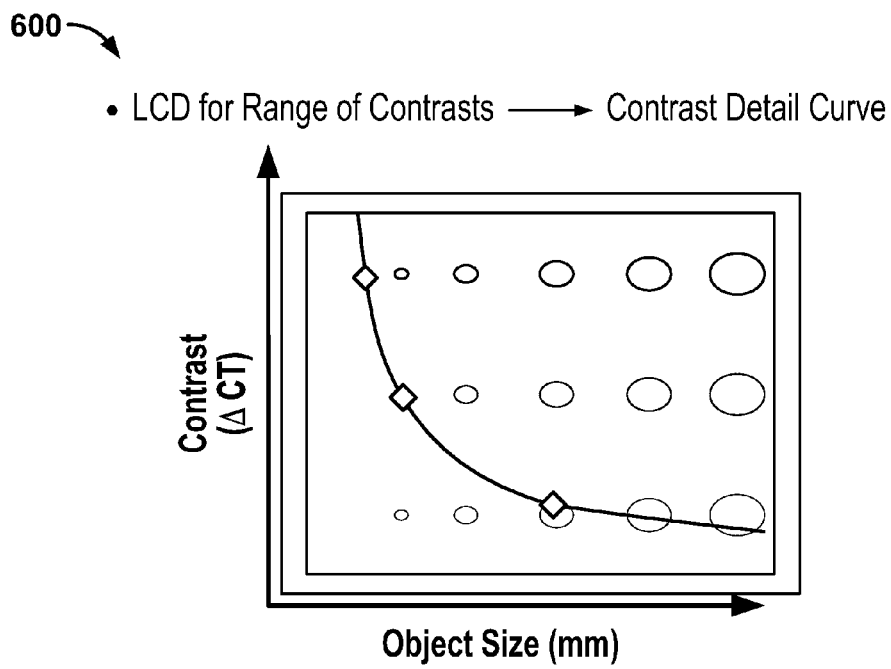
FIG. 6 depicts image quality based on radiation dose.

FIG. 6 depicts image quality based on radiation dose 600. See http:www.impactscan.org/slides/impactcourse/noise_and_low_contrast_resolution/index.html. The quality of a given CT image depends on a number of factors, but for the purposes of minimizing radiation dose, image quality is dependent on radiation dose. As radiation dose decreases, quantum mottle effects are increased, degrading image quality, manifested by increased visual noise, which decreases target detectability. Thus, visual noise is a reasonable method of quantifying image quality, and is the method employed here.

Figure 7:
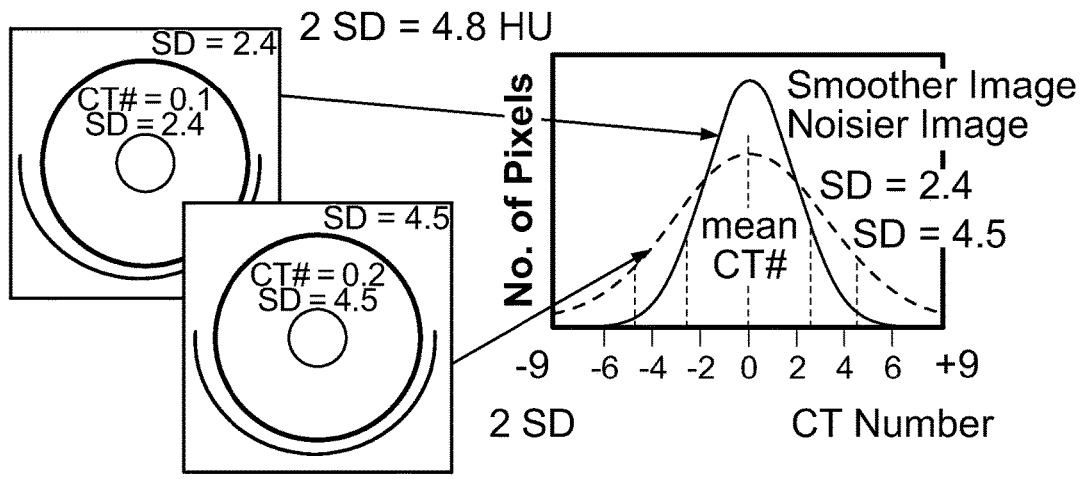
FIG. 7 shows visual noise measured as the standard deviation.

As shown in FIG. 7, visual noise, or noise, can be measured and charted 700 as the standard deviation of the CT units of a region that is known to be homogenous in x-ray density, See http:www.impactscan.org/slides/impact-course/noise_and_low_contrast_resolution/index.html.

Figure 8:
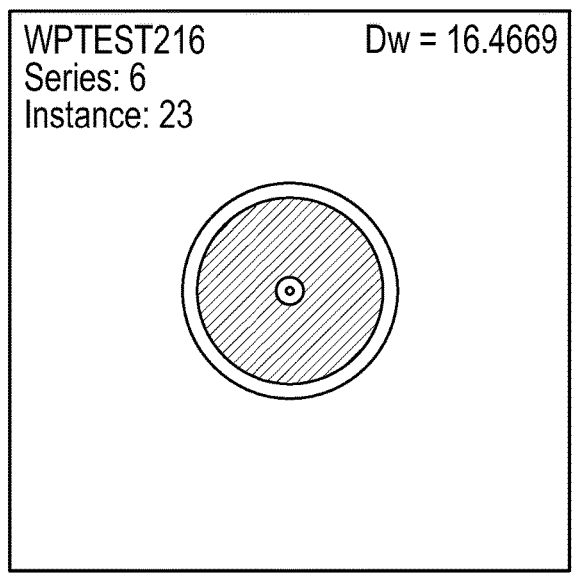
FIG. 8 shows image noise centroid and standard deviation of this region.

To determine the relationship between image noise, tube current, and $D_W$, the conical water phantom was scanned at a constant kV and effective mAs and noise was measured in a 3-cm-diameter circular region of interest at the isocenter of a 5 mm slice at a measured cross-sectional diameter displayed as 800 in FIG. 8. Image noise was defined as the standard deviation of Hounsfield units (HU) within the region of interest. Images were generated using filtered back projection technique and a standard soft-tissue convolution kernel without de-noising or other post-acquisition image processing. A mathematical model was then empirically derived and fit to the data to provide image quality estimates over a range of patient sizes and radiation doses.

Conical phantom noise measurements were performed at various voltage potentials (80, 100, 120, 135 kV) and tube current settings (50, 100, 150, . . . , 500 mA) and using various scan modes and parameter settings, including acquisition mode, focal spot size, and bowtie filter. Appropriate constants were generated by fitting the model to the data at each setting. Correlation coefficients were used to evaluate the accuracy of the model at each setting.

Figure 9:
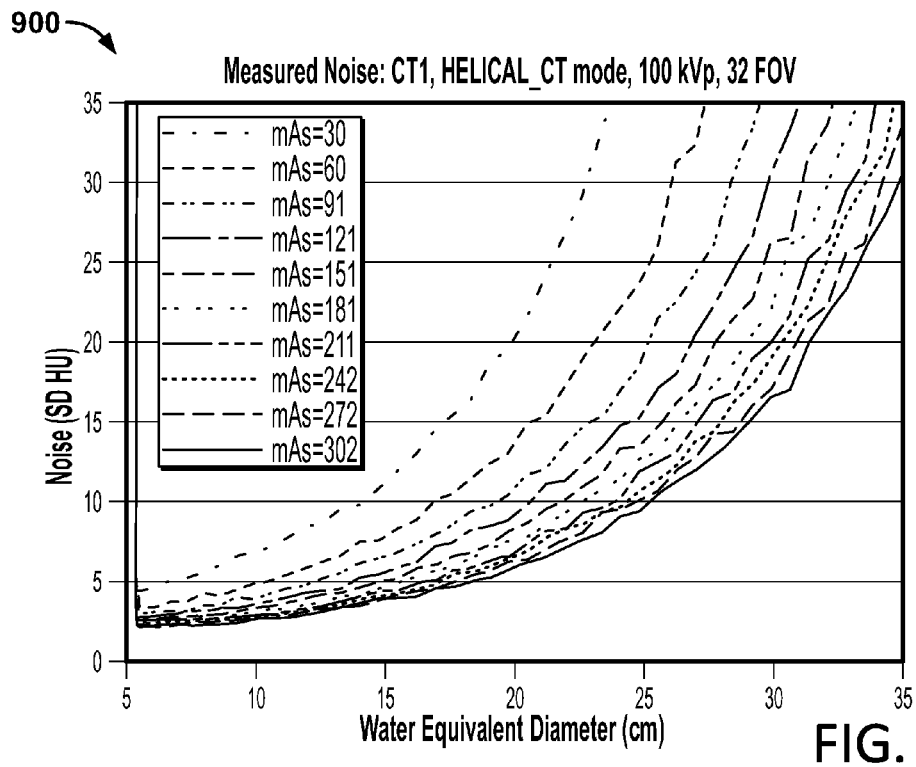
FIG. 9 shows a chart of noise measured from a conical phantom.

FIG. 9 shows noise measured from the conical phantom of Water Equivalent diameter at the varied levels of mAs. Noise can be directly measured from images obtained from scans of cylindrical or conical water phantoms of known diameter. The noise measurements obtained from the conical water phantom were modeled 900 according to the following equation:

$$\sigma = c_0 + c_1 (c_{m_e} m_e)^{c_2} e^{[D_W c_3 (c_{m_e} m_e)^{c_4}]}$$

where $\sigma$ is noise, $c_0$, $c_1$, $c_2$, $c_3$, $c_4$, and $c_{me}$ are empirically-derived constants and $m_e$ is effective $$mAs = \frac{mA \cdot (\text{rotation time})}{\text{pitch}}.$$

Figure 10:
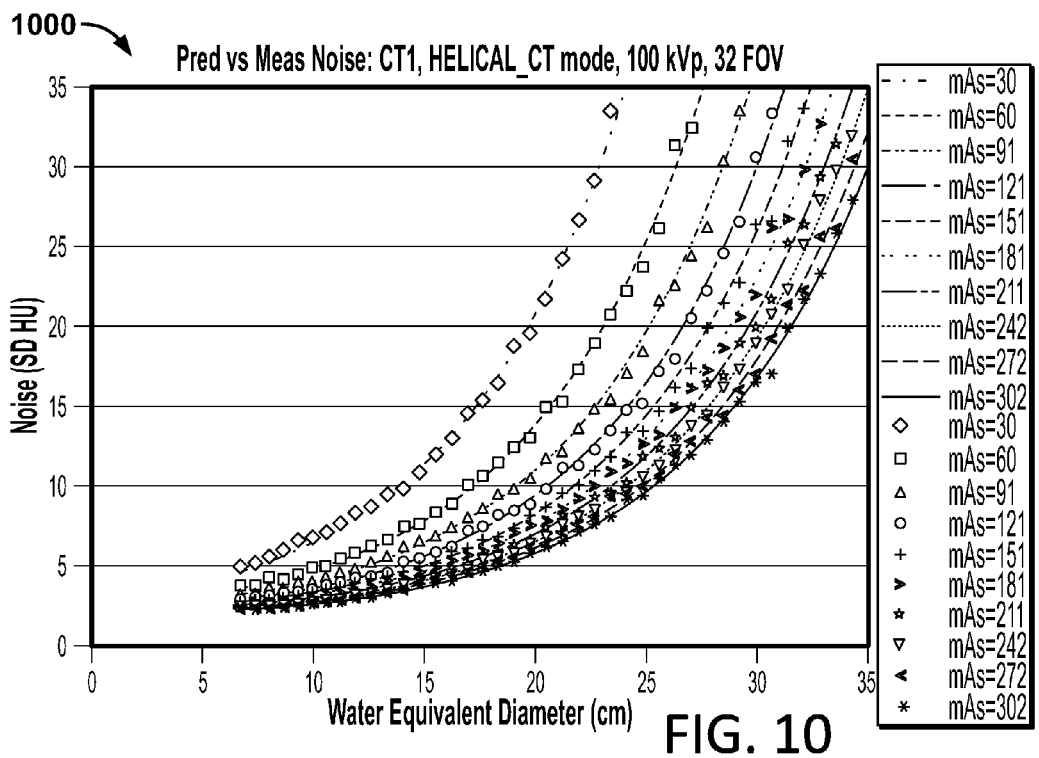
FIG. 10 shows a chart of noise, including the measured data, as well as the fitted model curve.

An example is shown in FIG. 10, which includes both the measured data shown in FIG. 9 as well as the fitted model 1000. Terminology for the model constants is arbitrary and can be changed.

Figure 11:
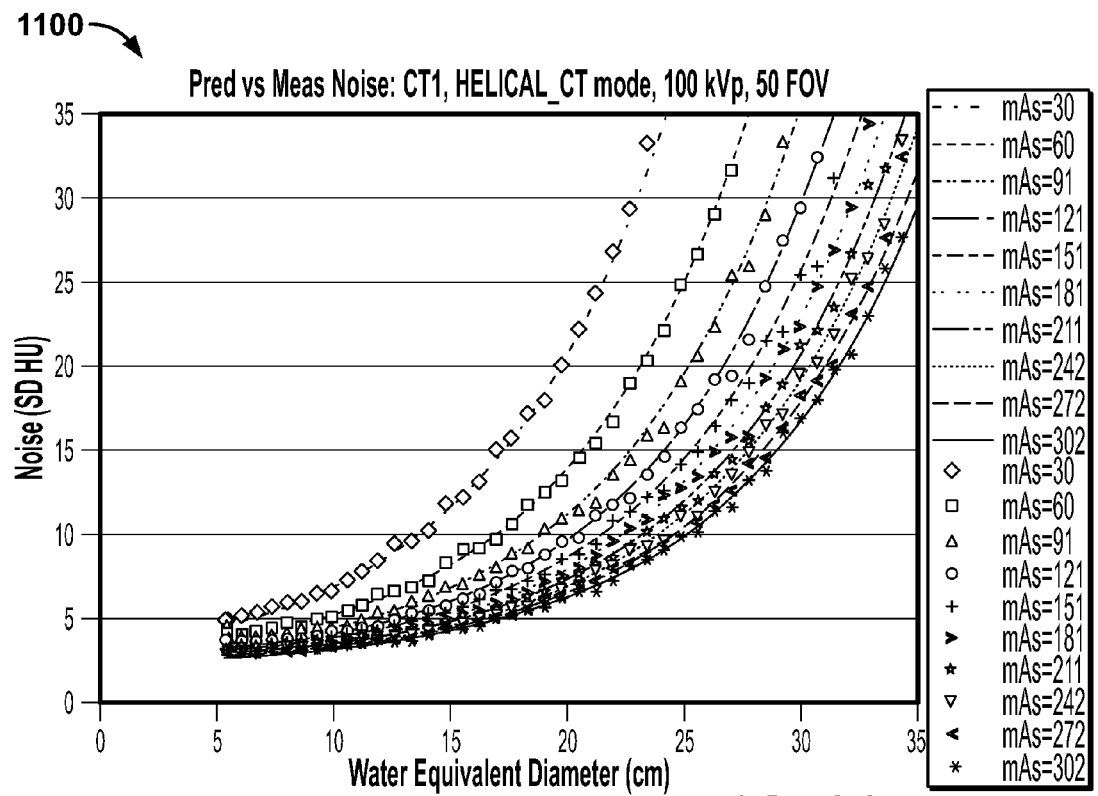
FIG. 11 shows a chart of predicted image quality for a water equivalent diameter.

Noise is a function of the radiation dose parameters (including kV and mAs), water-equivalent diameter of the subject, and scanner characteristics, such as scan mode, bowtie filter, focal spot size, detector efficiency, etc. Some of these factors are inherent in the scanner, and, thus, fixed for all scans on the scanner. Others can be changed, such as kV, scan mode, bowtie filter and focal spot size. Therefore, a different set of constants may be derived for each setting. FIG. 11 predicts image quality in a chart 1100 for field of view of 50 cm. See Seuss C, in Mahesh M, MDCT Physics: The Basics, 2009, p 135.

Empirical measurements showed that, $c_0$, $c_1$, $c_2$, $c_3$, and $c_4$ can be treated as constant for the scanner, with a relatively small amount of error. However, $c_0$, and $c_{me}$ change, depending on the settings. For example, in the Toshiba Aquilion One, these values change for different kV levels (4 settings), different scan modes (3 settings), and different data collection diameters (5 settings). In order to avoid deriving different values of $c_0$ and $c_{me}$, for the 60 permutations of these settings, two correction factors, $cf_{Co}$, and $cf_{Cme}$, are also incorporated into the model by multiplying these correction factors by $c_0$ and $c_{me}$, respectively. This is done by establishing constants for an arbitrarily-chosen "standard scan setting," with specified kV, scan mode, and data collection diameter settings, for example. Appropriate $c_0$ and $c_{me}$ values are derived for each setting, keeping all other settings constant. For example, for the Toshiba Aquilion One, the "typical scan" settings used for the model were mode=helical, kV=100, and data collection diameter=32 cm. The $c_0$ and $c_{me}$ values for this setting were found to be 1.41 and 0.0242, respectively. The correction factors $cf_{Co}$, and $cf_{Cme}$ for 120 kV were found to be 1.24 and 1.90, respectively, which were then multiplied by the standard $c_0$ and $c_{em}$ values, resulting in corrected $c_0$ and $c_{me}$ of 1.75 and 0.0460, respectively.

For studies using the anterior-posterior (AP) topogram, the method described above does not incorporate the CT table into the water-equivalent diameter calculation. Therefore, for these studies, constants in the noise model may be obtained from images using phantoms that were on the table. However, for those that depend on a lateral topogram only, constants in the noise model may be obtained from phantoms that extended off of the end of the table.

Following development of the image noise estimation models, patient size data were extracted from the topogram and then combined with dose parameters to estimate the image noise at each scan level. To validate these estimates on simulated patients, axial scans were performed on two rudimentary anthropomorphic phantoms constructed to simulate child and adult torsos, with average water-equivalent diameters of 14.1 and 21.3 cm, respectively. A 6-cm diameter water column was inserted longitudinally through the center of the phantoms and image noise measurements were obtained at the isocenter of the cross-section. Actual noise measurements were compared to the predicted noise based on the noise model described above. This process was performed 16 times, on the pediatric and adult phantoms, on the two scanners at 100 and 120 kV, with and without dose modulation, and at various tube current settings. Non-paired t-tests were used to compare the accuracy of image noise predictions of child vs. adult phantoms, 320-vs. 64-detector row scanners, and modulated vs. fixed tube current.

Table 1 lists the results of the comparison of predicted to measured noise on the validation scans of the rudimentary anthropomorphic phantoms. Overall, the model slightly underpredicted noise by approximately 0.74 (+/−0.66) SD HU, which was equivalent to 5.7% (+/−4.5%) of the measured noise. There was no significant difference in prediction accuracy between the 320- and 64-detector row scanners or between modulated and fixed tube current. The model underpredicted noise on the adult phantom more than on the child phantom.

TABLE 1

| n | Phantom | Scanner | Tube Current Modulation | Mean Predicted Noise (SD HU) | Mean Measured Noise (SD HU) | Mean Predicted − Measured Noise (SD HU) |
|---|---|---|---|---|---|---|
| 2 | Child | 320-slice | Modulated | 8.91 | 9.12 | −0.21 |
| 2 | Child | 320-slice | Fixed | 9.67 | 9.63 | 0.04 |
| 2 | Child | 64-slice | Modulated | 9.20 | 9.88 | −0.68 |
| 2 | Child | 64-slice | Fixed | 8.38 | 8.63 | −0.25 |
| 2 | Adult | 320-slice | Modulated | 12.88 | 13.70 | −0.81 |
| 2 | Adult | 320-slice | Fixed | 15.77 | 16.48 | −0.70 |
| 2 | Adult | 64-slice | Modulated | 10.18 | 11.49 | −1.30 |
| 2 | Adult | 64-slice | Fixed | 14.33 | 16.34 | −2.01 |
| 8 | Adult | All | All | 9.04 | 9.32 | −0.27* |
| 8 | Child | All | All | 13.29 | 14.50 | −1.21* |
| 8 | All | 320-slice | All | 11.81 | 12.23 | −0.42 |
| 8 | All | 64-slice | All | 10.52 | 11.59 | −1.06 |
| 8 | All | All | Modulated | 10.30 | 11.05 | −0.75 |
| 8 | All | All | Fixed | 12.04 | 12.77 | −0.73 |
| 16 | All | All | All | 11.17 | 11.91 | −0.74 |

CT dose index (volume), or $CTDI_{vol}$, is an estimate of radiation dose given to an individual undergoing CT.

$CTDI_{vol}$ calculations are based on either a 16 cm or 32 cm polymethyl methacrylate (PMMA) phantom. For the purposes of this discussion, all $CTDI_{vol}$ calculations are based on, or converted to those based on, the 32 cm PMMA phantom. $CTDI_{vol}$ is reported by the scanner in the dose report, an image generated at the end of a CT study. However, this information is often not available as a DICOM header, and thus utilizes an optical character recognition (OCR) application to automate data acquisition. Furthermore, the dose report may be inaccurate in that the reported $CTDI_{vol}$ may not accurately account for fluctuating dose which occurs in dose modulation.

The model used the size-specific dose estimate (SSDE) for the measure of radiation dose estimates, which is derived from the estimated patient size and the CT dose index ($CTDI_{vol}$), according to the following equation. (Boone AAP cM TG 204 2011)

$$SSDE = (a \cdot e^{-b \cdot D_W}) CTDI_{vol}$$

The model's estimates for $CTDI_{vol}$ were derived from the manufacturer's estimates. For each combination of scan mode, voltage potential, bowtie filter, and focal spot size, a ratio of $CTDI_{vol}$ to effective mAs was determined and incorporated into the model in order to estimate individual study $CTDI_{vol}$ based on information available in the DICOM metadata. Accuracy of the $CTDI_{vol}$ estimates was validated using 30 randomly-selected CT chest, abdomen, and pelvis examinations, half on the 320-detector row scanner and half on the 64-detector row scanners. The $CTDI_{vol}$ estimates derived from the model were compared to those in the manufacturer's dose report page. Mean study $CTDI_{vol}$ was used for the 320-detector row scanner and the maximum $CTDI_{vol}$ was used for the 64-detector row scanner in order to mirror the information provided in the manufacturer's dose report.

Of the 30 CT chest, abdomen, and pelvis studies used to validate the accuracy of the $CTDI_{vol}$ estimation, the mean estimated $CTDI_{vol}$ was 6.10+/−3.10 mGy. The mean $CTDI_{vol}$ reported by the manufacturer's dose sheet was 6.06 mGy+/−3.02 mGy. The mean difference between estimated and reported $CTDI_{vol}$ was 0.04+/−0.10 mGy. The mean percent difference between estimated and reported $CTDI_{vol}$ was 0.8%+/−1.8%. Of note, by using the maximum rather than the mean $CTDI_{vol}$ on the 64-detector row scanner, the manufacturer overestimated the $CTDI_{vol}$ by an average of 0.85 mGy, corresponding to an average percent overestimate of 15.0%.

Target Image Noise Estimation

Figure 12:
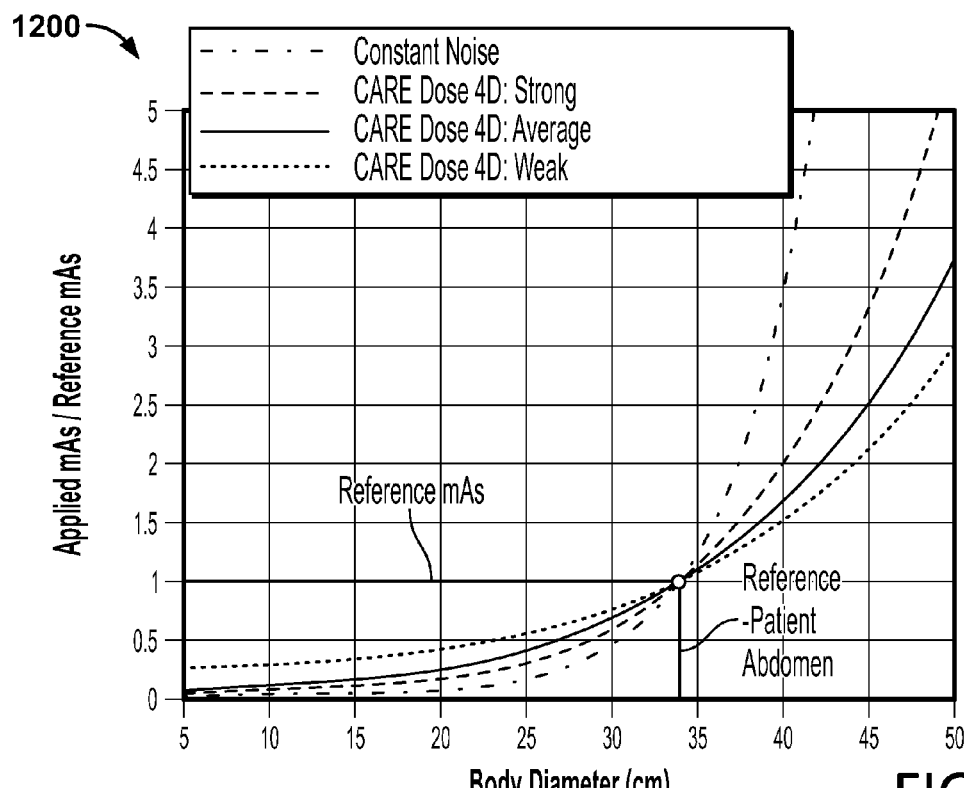
FIG. 12 shows a chart of target image quality doses based on patient size.

CT manufacturers have described a reproducible phenomenon among practicing radiologist: radiologists can tolerate different levels of noise for patients of different sizes. For example, FIG. 12 illustrates Seimen's CARE Dose system of automatic exposure control. This likely is due to the fact that larger patients have larger organs, requiring less fine spatial resolution, and larger patients tend to have larger amounts of fat, providing greater contrast resolution. FIG. 12 shows Target Image quality doses 1200 derived based on patient size. Image quality is prospectively estimated and parameters for image quality are prospectively determined.

Therefore, a constant noise cannot be used to establish target image quality. Rather, a target image noise curve should be established over a range of patient sizes. In order to determine target image noise curves, radiologist image quality preferences should be established. To quantify radiologist preferences, a 5-point scoring system can be used, according to Table 2.

TABLE 2

| Score | Diagnostic quality | Explanation |
|---|---|---|
| 1 | Non-diagnostic quality with high level of noise | You would recommend that the examination be repeated. |
| 2 | Borderline diagnostic quality with high level of noise | You would probably not repeat the examination, but you consider the study to be "barely passable" and might recommend using a higher dose next time. |
| 3 | Acceptable diagnostic quality with moderate level of noise | The dose is adequate but does not appear to be excessive. The dose possibly could be lowered and still be of diagnostic image quality, but it should not be reduced by much. |
| 4 | Good diagnostic quality with low-to-moderate level of noise | The dose probably could be lowered and still be of diagnostic image quality. |
| 5 | Excellent diagnostic quality with low level of noise | The dose definitely could be lowered and still be of diagnostic image quality. |

Radiologists can rate images of known noise and $D_W$ to assign an image quality preference score for the image.

Figure 13:
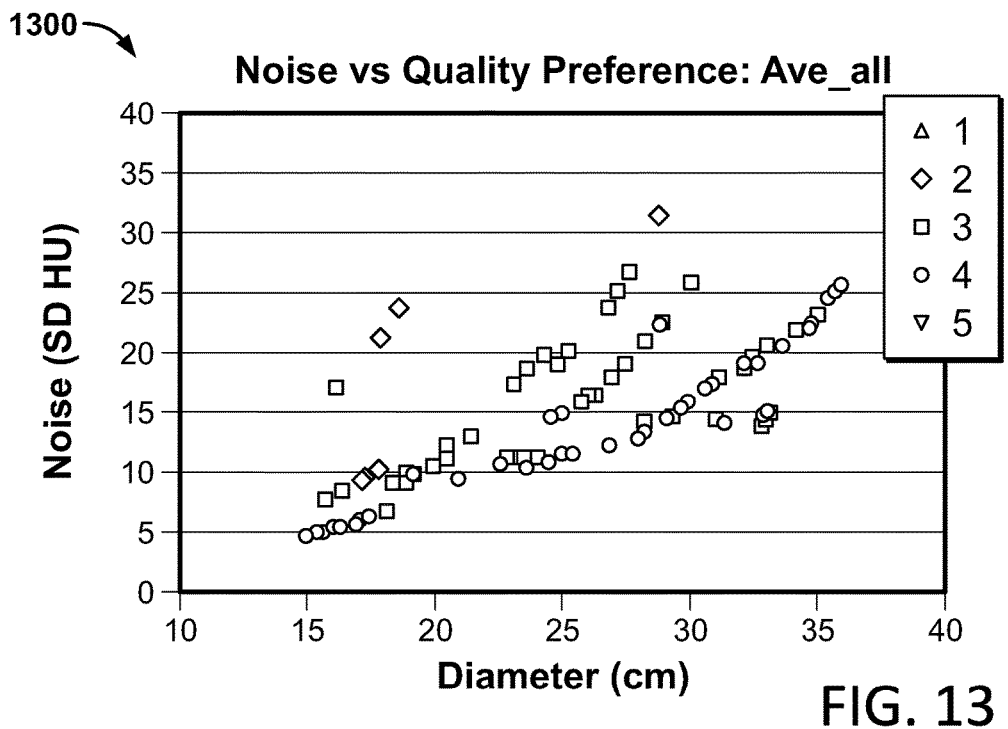
FIG. 13 shows a plot of scored cases of known image noise and $D_W$.

Images of a range of patient sizes and image quality can be rated by radiologists, according to the 5-point scoring system. These can be obtained for an individual radiologist and/or averaged for a group of radiologists. Cases can be selected according to the typical exam for which the target image noise curve is to be applied. Cases are presented for scoring following all image post-processing techniques that would be applied in the clinical setting. The scored cases of known image noise and $D_W$ can be plotted 1300 as shown in FIG. 13.

Figure 14:
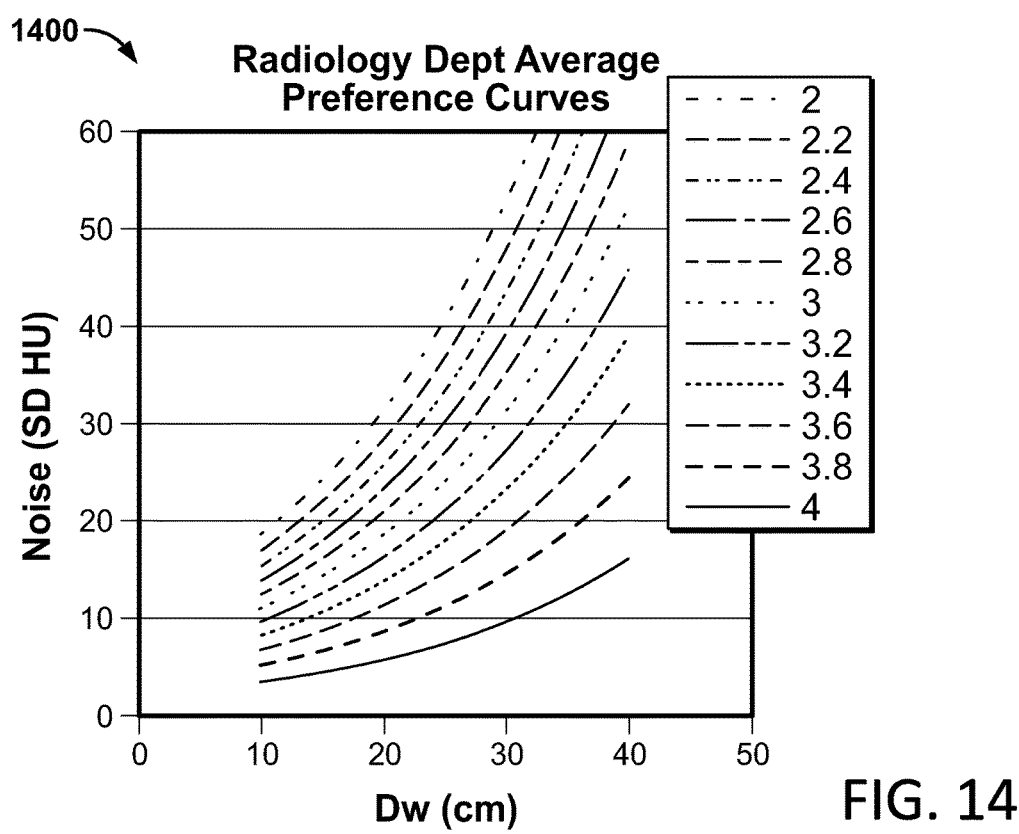
FIG. 14 shows a series of target image noise curves, according to the preference score.
Figure 15:
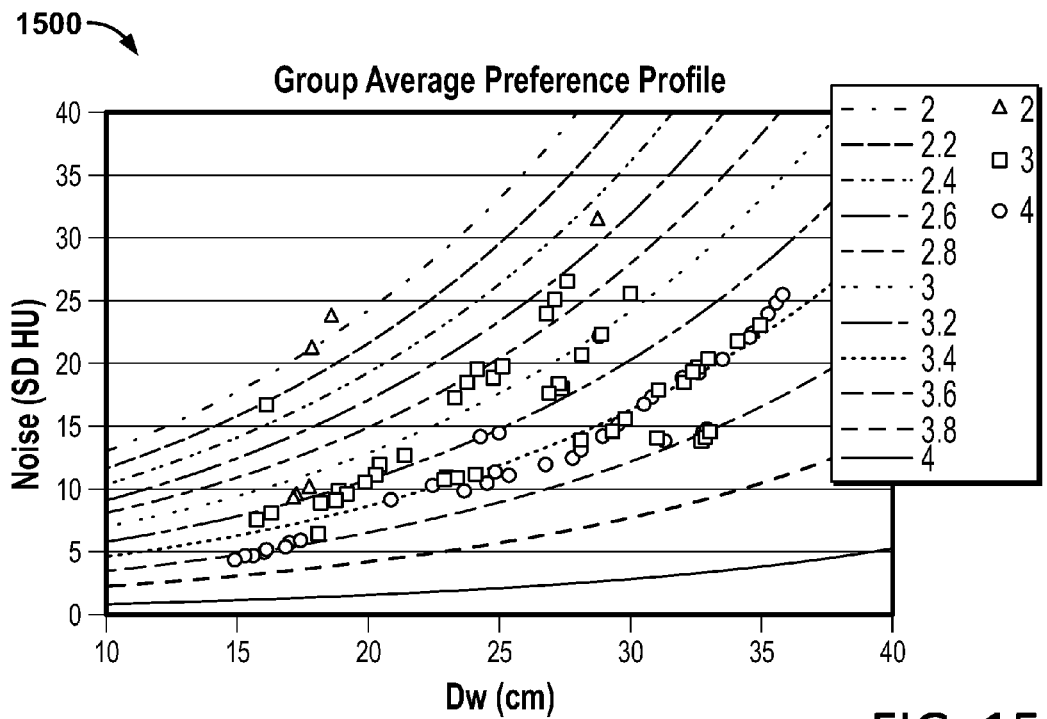
FIG. 15 shows a noise v. quality score radiologist preference mapped to a chart.

Using the a least absolute deviation method, scored cases can be fitted to an image quality preference profile equation:

$$S = 1 + \frac{4}{\left[1 + Ae^{(B\sigma e^{-CD_W})}\right]}$$

where S is the image quality preference score, σ is image noise, $D_W$ is patient size data, and A, B, and C are empirically-derived constants. This equation results in a series of target image noise curves, according to the preference score 1400, as shown in FIG. 14. This can be mapped to the scored cases data 1500 as shown in FIG. 15.

Figure 16:
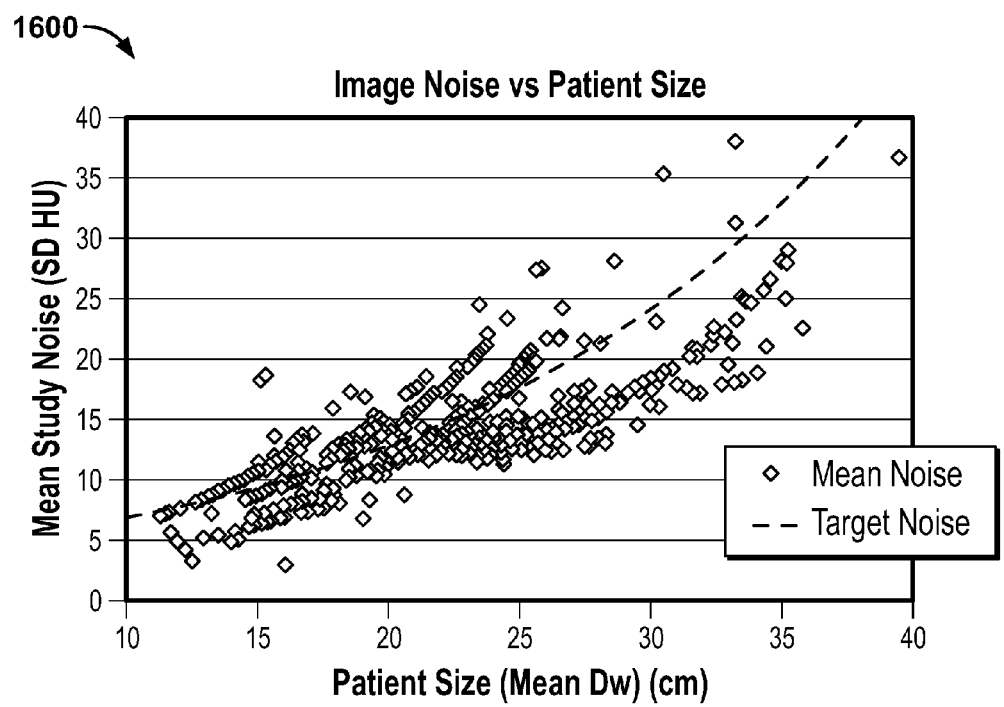
FIG. 16 shows a Target Image Quality curve set over a range of patient sizes.

Based on the desired image quality for examinations of a given indication or protocol, a target curve 1600 shown in FIG. 16 can be established by establishing a constant image quality preference score over a range of patient sizes, according to the following equation:

$$\text{Target noise} = c_T + a_T \cdot e^{b_T} \cdot e^{b_T D_W}$$

where $c_T$, $a_T$, and $b_T$ are empirically-derived constants. Separate target noise curves, with their corresponding constants, are derived for each clinical indication or set of protocols. These curves may be based on radiologists' subjective assessment of appropriate image quality for that equation.

Because radiologists tend to have varied levels of noise tolerance, a unique image quality preference profile may be generated for each radiologist. A group's image quality preference profile is created by averaging all radiologist's scores for each image and fitting the model. Each radiologist's profile can be compared to the overall department profile by determining the average score of the individual radiologist's preference curve that corresponded to the department's "3" preference curve for $D_W$=10 through 40 cm. The difference between these numbers is termed the Relative Acceptability Profile (RAP) score. A negative score indicates that the radiologist tolerates less noise than the group average and a positive score indicates that the radiologist tolerates more noise than the group average.

Prediction and Optimization Models
Dose Modulation Estimation

Most modern CT scanners are capable of applying tube current dose modulation, which automatically changes the tube current as the gantry moves in order to minimize the radiation dose. Z-axis tube current modulation may be applied as the patient moves through the gantry and angular, or x-y, modulation may be applied as the gantry rotates around the patient. The operator sets all other settings, as well as tube current modulation settings such as a target noise setting and a minimum and maximum mA, and the CT scanner determines the optimal radiation dose based on the attenuation data from the topogram. While dose modulation allows for dose optimization, it does not ensure it, since the key driver of dose—the tube current—remains under the operator's control via the target noise setting.

The dose modulation algorithm is programmed into the scanner. If the manufacture does not provide this algorithm for incorporation into this system, an approximation can be determined empirically by scanning elliptical phantoms of various sizes at various scanner settings, including kV and mAs. Minimum and maximum mA values can be determined for each phantom size and at each setting and evaluated to determine an approximation for the dose modulation algorithm.

Variable-sized ellipsoid phantoms were used to derive a model of the dose modulation algorithms of the scanners, predicting average mA for a given patient size at specified dose modulation parameter settings. The image noise estimation model described above was used to develop a prediction model, enabling the estimation of image noise and SSDE given patient size and scan parameters. An iterative non-linear optimization routine (Excel, Microsoft Corp, Redmond, Wash.) enabled the model to also do the reverse: provide recommended dose parameters given desired image quality targets and patient size. The model incorporated patient size, which could be derived from the scout topogram image, could be entered directly, or could be based on patient weight (in which case the model estimated patient size based on a given weight). The model also took into account specific parameters unique to the scanner. Tube current settings could be entered as fixed mA or dose modulation parameters. The user could also specify a target noise setting or image quality preference curve. Based on the information provided, the model then predicted image noise and dose estimates and recommended protocol parameters, including tube current and dose modulation settings, needed to achieve the desired image quality. Image noise and SSDE were also predicted over a range of patient sizes.

Image Noise and Dose Prediction Model

Figure 17:
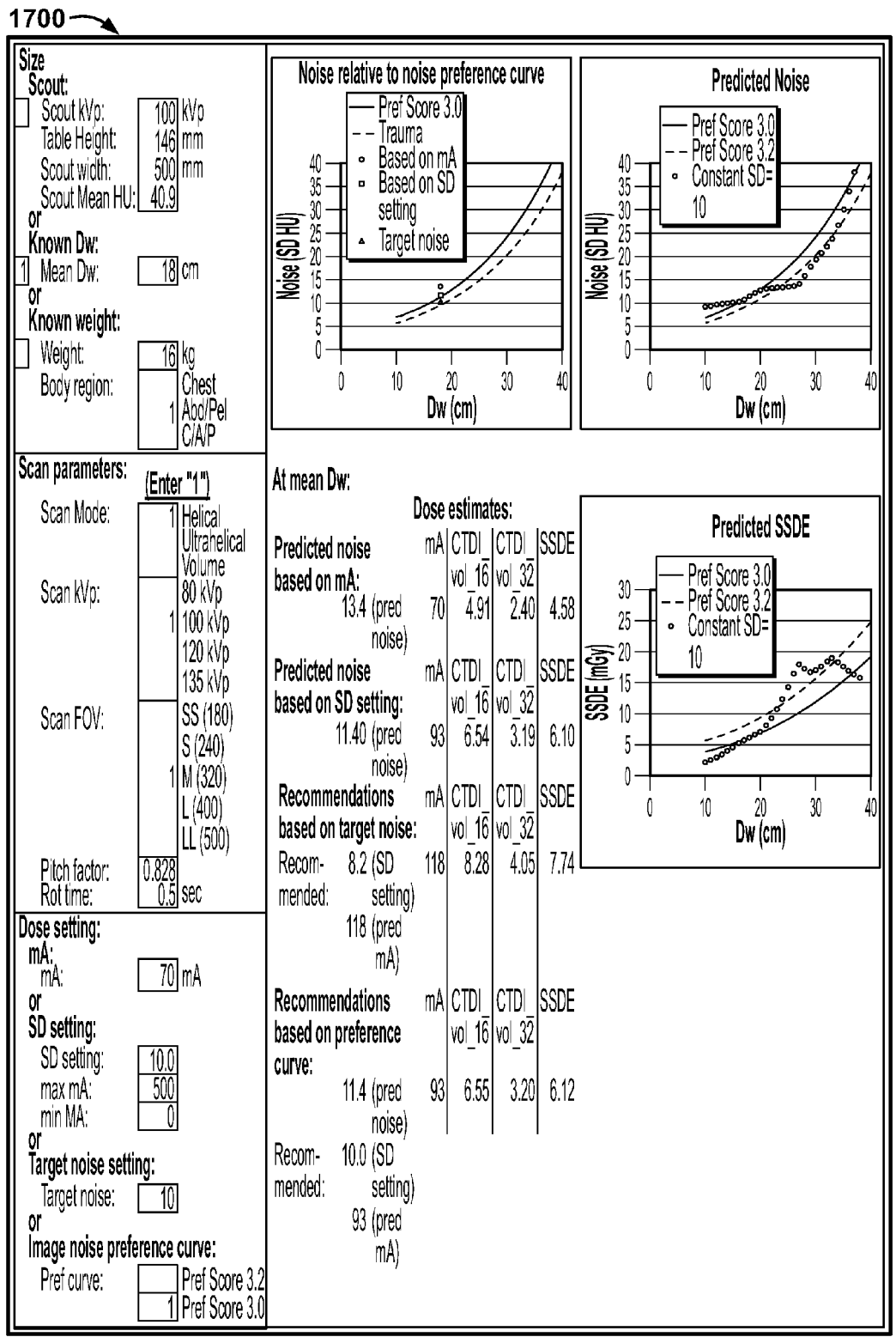
FIG. 17 shows a screen shot of the prediction application.

A single model may be used to predict image noise based on patient size and scanner parameters. The dose modulation algorithm is incorporated into the model to predict mAs based on dose modulation and other scan parameters and patient size entered into the model. The image noise equation may be used to predict image noise based on the mAs and other scan parameters and patient size. The target curve equation may be incorporated into the model to compare predicted image noise to actual image noise. Image noise is estimated over a range of patient sizes. This model is incorporated into a single application. A screen capture 1700 of the application is shown in FIG. 17. Image noise is simultaneously estimated using inputs of fixed mA and dose modulation settings.

The same application may be used to predict SSDE based on scan parameters and patient size. The $CTDI_{vol}$ and SSDE equations are incorporated into the prediction application. SSDE can estimated over a range of patient sizes at various modes of operation. The scan mode at which the lowest SSDE is found while keeping image noise constant is considered to be the lowest-dose mode. Once the lowest-dose scan mode is established, values for other scan parameters are entered into the application. SSDE is estimated over a range of patient sizes at the given scan parameter settings, as shown in FIG. 17.

The prediction model, including the dose modulation algorithm, was validated on a sample of 43 routine CT abdomen and pelvis studies performed on the three scanners by comparing the predicted vs. actual mean effective mAs, SSDE, and estimated image noise on 43 routine chest, abdomen, and pelvis examinations. 20 studies were performed on the 320-detector row scanner and 23 studies were performed on the 64-detector row scanner. 25 of the studies were performed at 100 kV and 18 studies were performed at 120 kV. All validation studies were performed in helical mode. Statistical significance of predictive accuracy between scanners and tube potential settings was assessed using non-paired t-tests.

The sample of 43 CT examinations used to validate the prediction model included studies with patient sizes, effective mAs, SSDE, and estimated image noise values ranging from 16.3-37.3 cm, 30-169 mAs, 3.4-16.1 mGy, and 9.4-38.2 SD HU, respectively. The mean differences between predicted and actual effective mAs, SSDE, and estimated image noise were −0.7+/−6.9 (SD) mAs, −0.2+/−0.9 mGy and −0.1+/−0.8 HU, respectively. Percent differences between predicted and actual values were −0.9%+−9.3%, −1.8%+/−10.6%, and −0.5%+/−4.4%, respectively. There were no statistically significant differences in predictive accuracy between the two scanners or between 100 and 120 kV.

Image Quality and Dose Optimization/Guidance Model

Image noise may be optimized over a specific range of patient sizes using the image noise and dose prediction model by superimposing the predicted image noise curve upon the target image noise curve. Image noise is predicted by adjusting dose modulation parameters until the image noise matches the target noise curve 1800, as shown in FIG. 18.

This optimization is automated by using a non-linear optimization routine to minimize the difference between the target image noise and the predicted image noise over a specified range of patient sizes by changing dose modulation parameters. Through the same optimization routine, the application also recommends specific tube current modulation settings and fixed mA settings that are predicted to result in noise that matches a single desired image noise or the target image noise curve.

Figure 18:
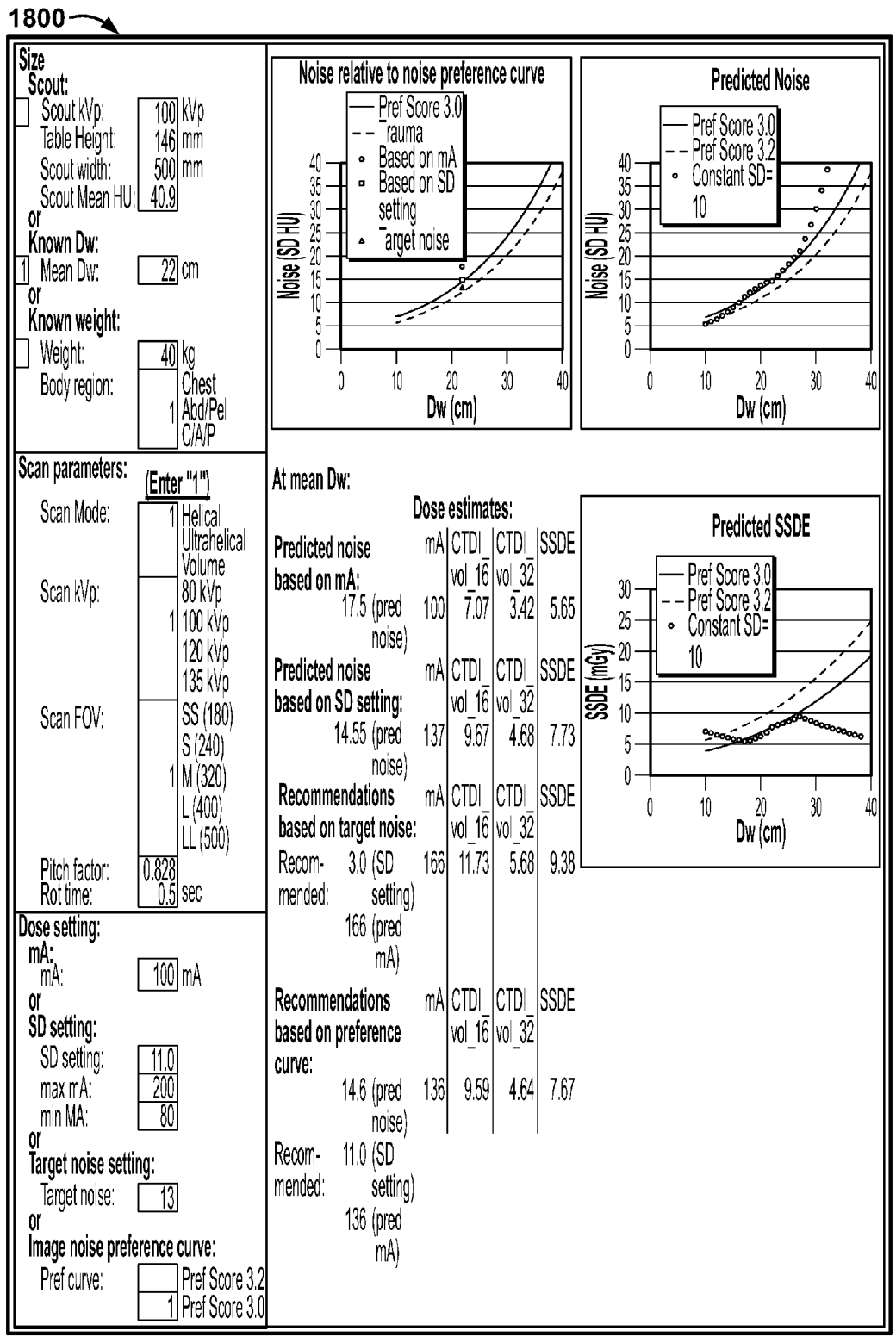
FIG. 18 shows screen shot of the prediction application.

Predicted SSDE is displayed and plotted at the optimized image quality settings, as shown in FIG. 18. The constraint in this optimization model is image noise rather than radiation dose. Therefore, the model does not change scan parameters to match a desired SSDE; rather, the SSDE is a result of the scan parameters established to match a desired image noise target.

Scan parameters are derived from the prediction/optimization application to optimize dose for ranges of patient size to match appropriate target image noise curves based on clinical indications. These scan parameters are used to determine scan protocols, which are entered into the scanner. An example of a group of protocols is shown in Table 3.

TABLE 3

Guidance Protocols
Updated Apr. 2, 2012

| Size | Mode | FOV | mm | kV | Rot time | SD | mA max | mA min |
|---|---|---|---|---|---|---|---|---|
| 320-detector CT | | | | | | | | |
| Body | | | | | | | | |
| 0-15 kg | Vol | S | 200 | 100 | 0.35 | 24 | 160 | 100 |
| 16-30 kg | Hel | M | 260 | 100 | 0.5 | 10 | 170 | 70 |
| 31-45 kg | Hel | M | 300 | 100 | 0.5 | 11 | 200 | 80 |
| 46-70 kg | Hel | M | 320 | 100 | 0.5 | 13 | 280 | 110 |
| 71-100 kg | Hel | L | 400 | 120 | 0.5 | 17 | 220 | 90 |
| 100+ kg | Hel | LL | 500 | 120 | 0.5 | 24 | 380 | 140 |
| Trauma | | | | | | | | |
| 0-15 kg | Vol | S | 200 | 100 | 0.35 | 20 | 180 | 100 |
| 16-30 kg | Hel | M | 260 | 100 | 0.5 | 8 | 220 | 90 |
| 31-45 kg | Hel | M | 300 | 100 | 0.5 | 10 | 300 | 130 |
| 46-70 kg | Hel | M | 320 | 100 | 0.5 | 11 | 400 | 160 |
| 71-100 kg | Hel | L | 400 | 120 | 0.5 | 14 | 260 | 110 |
| 100+ kg | Hel | LL | 500 | 120 | 0.5 | 20 | 440 | 200 |
| 64-detector CT | | | | | | | | |
| Body | | | | | | | | |
| 0-15 kg | Hel | S | 200 | 100 | 0.5 | 12 | 70 | 40 |
| 16-30 kg | Hel | M | 260 | 100 | 0.5 | 15 | 120 | 60 |
| 31-45 kg | Hel | M | 300 | 100 | 0.5 | 16 | 170 | 60 |
| 46-70 kg | Hel | M | 320 | 100 | 0.5 | 17 | 200 | 70 |
| 71-100 kg | Hel | L | 400 | 120 | 0.5 | 23 | 160 | 80 |
| 100+ kg | Hel | LL | 500 | 120 | 0.5 | 28 | 220 | 90 |
| Trauma | | | | | | | | |
| 0-15 kg | Hel | S | 200 | 100 | 0.5 | 12 | 70 | 40 |
| 16-30 kg | Hel | M | 260 | 100 | 0.5 | 12 | 180 | 70 |
| 31-45 kg | Hel | M | 300 | 100 | 0.5 | 12 | 200 | 70 |
| 46-70 kg | Hel | M | 320 | 100 | 0.5 | 14 | 280 | 100 |
| 71-100 kg | Hel | L | 400 | 120 | 0.5 | 19 | 180 | 70 |
| 100+ kg | Hel | LL | 500 | 120 | 0.5 | 24 | 280 | 110 |

The prediction/optimization model can incorporate a $D_W$ value or range entered by the user. Alternatively, the user can specify patient weight or weight range. The model uses a lookup table to determine expected $D_W$ based on patient weight, according to data from the patient population. Alternatively, the user may obtain patient size directly from the scout topogram image, which is performed prior to the axial acquisition. The prediction/optimization application contains the equations that convert density units from the topogram to patient size. An operator may select a rectangular region of interest from the topogram and enter the mean density unit value into the model, as well as the scout kV, table height, and the scout width, as shown in FIG. 18. The specific patient size may then be calculated based on the method described above. The model then calculates optimized tube current modulation parameter settings based on the target noise curve, which the operator may enter into the scanner prior to performing the axial acquisition.

The optimization model may be programmed into a prediction/guidance application 1800, in FIG. 18. The application incorporates all elements of the optimization model, providing the practical tool capable of predicting image quality and dose based on mA, dose modulation settings, specific target noise, and image quality preference curve based on a given patient size. The top left graph predicts image noise based on mA, dose modulation settings, and target noise, respectively, relative to image quality preference curves. The top right and bottom right graphs predict image noise and SSDEs over a range of patient sizes, respectively, based on the dose modulation model and relative to image quality preference curves.

As FIG. 18 illustrates, the predicted noise over a range of patient $D_W$ 10-40 cm at 100 kV and with a constant noise factor (SD) setting of 10.0 ranges from 9 to 55 SD HU. For the example shown, the noise remains relatively constant between 10 and 16 cm, increases between 17 and 21 cm, remains relatively constant between 21 and 26 cm, then increases rapidly between 27 and 33 cm (where the long-axis of the modulated tube current is limited by the maximum mA setting) and increases even more rapidly for 34 cm and above (where the tube current has reached the maximum setting in both axes). When compared to the "3.0" target noise curve, the predicted noise is excessively high for $D_W$ between 10 and 15 cm, appropriate between 16 and 20 cm, lower than necessary between 21 and 36 cm, and again excessively high above 36 cm. Correspondingly, the SSDE is higher than necessary for ranges where the noise is lower than necessary and vice versa.

Image Quality and Dose Performance Assessment, Display, and Monitoring

Image Processing

The exemplary image processing application (processor) opens each file in the folder automatically and, from the Digital Imaging and Communications in Medicine (DICOM) tags, determines whether it represents the topogram and then assesses other characteristics of the image, such as its orientation, slice thickness, and time that the image was acquired. Once the processor has determined which images are the topograms, it chooses the anteroposterior (AP) topogram 400 if one is present, such as the one shown above in FIG. 4. If no AP topogram is present, it chooses the lateral topogram 2200 such as the one in FIG. 22, which is often the case with head CTs.

The exemplary processor then performs a row-by-row integration of the topogram to determine $D_{W\_net}$ for each cross-sectional level along the z-axis. The application uses the DICOM header information to correlate the matrix rows with the physical location on the patient, which is then correlated with axial slice position. The average $D_W$ is also calculated and mapped 400 to the topogram image as shown in FIG. 4.

The exemplary processor then evaluates each series in the study and performs an algorithm to determine the appropriate axial images to use in determining dose calculations. For example, it discards all files that do not represent CT images. It also discards all coronal, sagittal, and other non-axial images. It assesses the time the study was performed to determine whether multiple series constitute reconstructed images of the same acquisition. It then determines which series are at slice intervals closest to 5 mm. If multiple series remain, it chooses the reconstruction series that was performed first.

The exemplary processor then assesses the dose parameters associated with each axial image. It assesses slice position, kV, mA, exposure time, pitch factor (if applicable), scan mode, and data collection diameter. It also assesses which scanner the study was performed on and accesses a data file to incorporate the appropriate constants into the calculations. Dose estimates, including $CTDI_{vol}$ and SSDE, are calculated at each level and averaged for the study.

Figure 19:
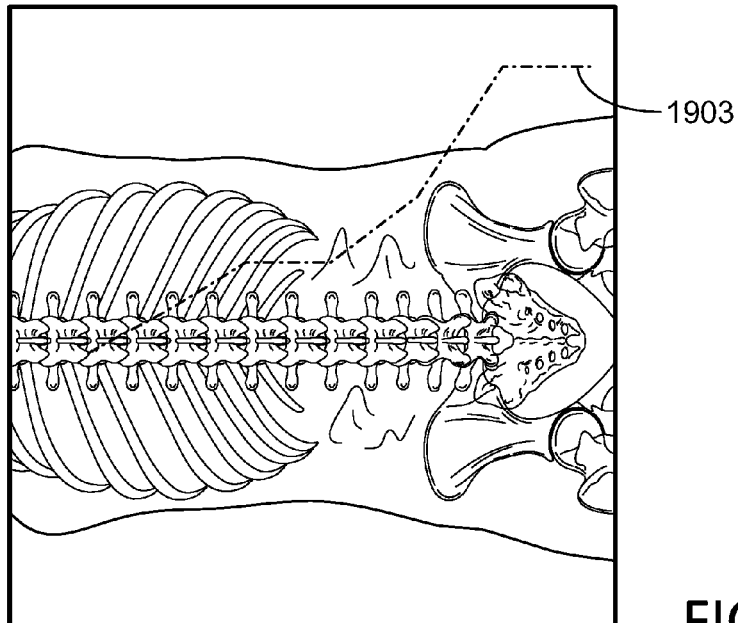
FIG. 19 shows an example AP topogram with effective mAs shown at each slice.

FIG. 19 shows a topogram 1900 with effective mAs determined 1903 at each slice as the product of mA, exposure time, and pitch factor. The processor may also calculate the percentage of the study along the z-axis where the mAs equals the maximum mAs (this has implications for whether the dose modulation settings are optimized or whether the maximum mA is set too low relative to the SD setting).

Figure 20:
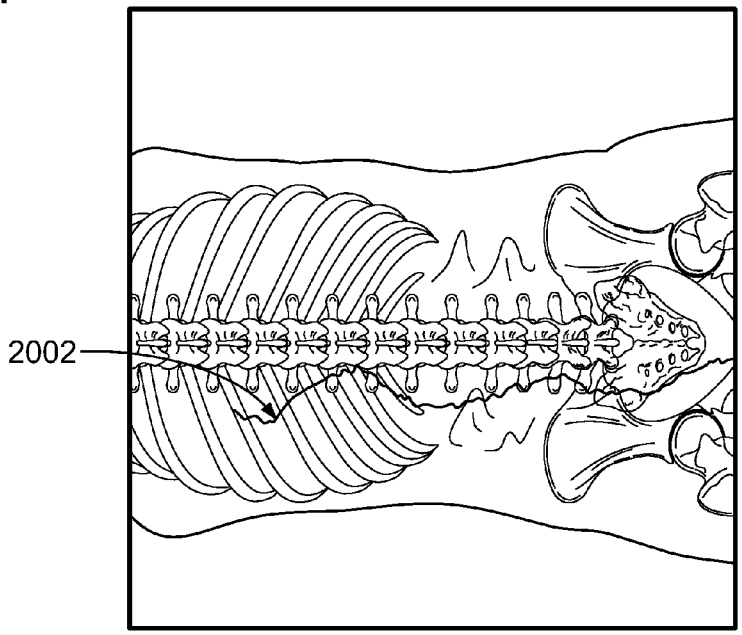
FIG. 20 shows an example AP topogram of estimated noise calculated at each slice.
Figure 21:
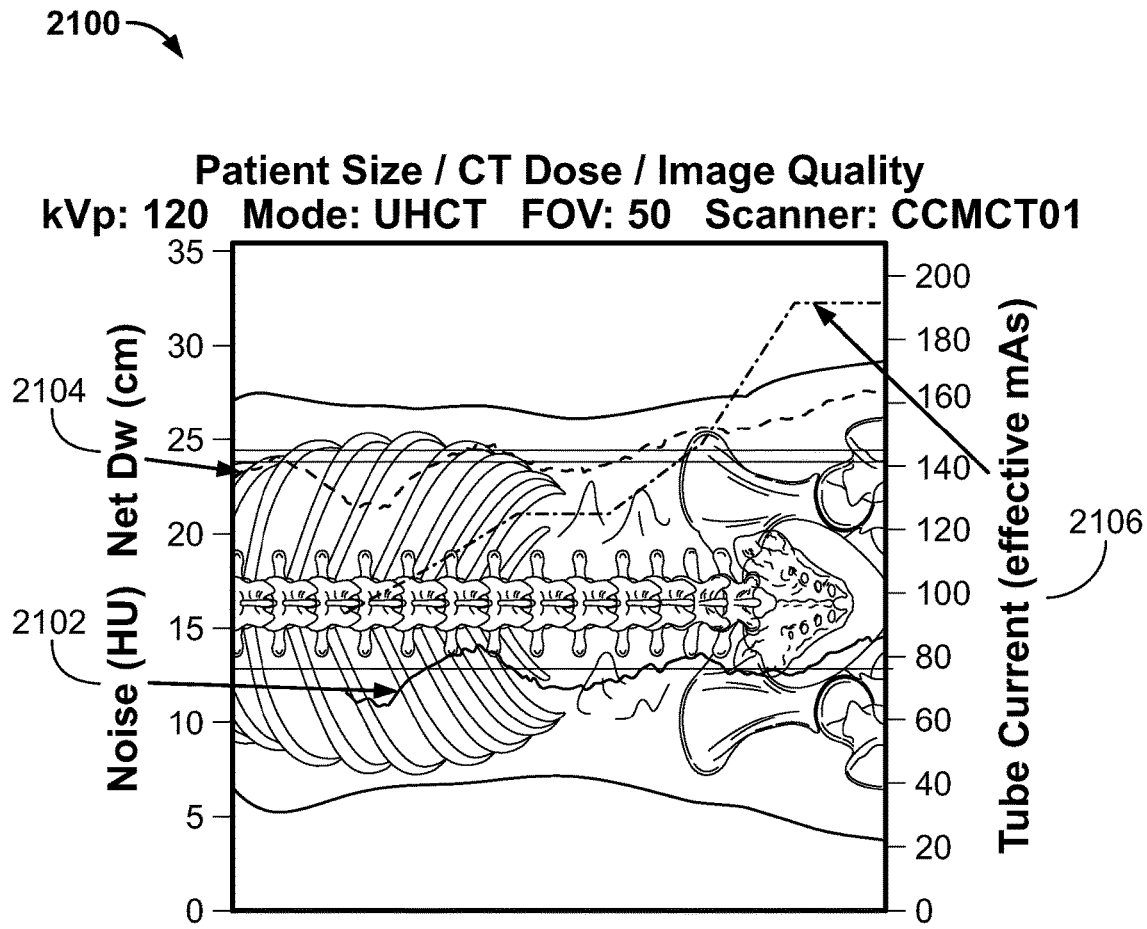
FIG. 21 shows $D_W$, mAs, and estimated noise mapped to an example AP topogram on a single image.

FIG. 20 shows an AP topogram 2000 of estimated noise calculated at each slice and mapped 2002 to a topogram 2000. Patient $D_W$ 2104, mAs 2106, and estimated noise 2102 are then all mapped to the topogram on a single image 2100, shown in FIG. 21. This image is saved in a dedicated folder and the processor retains the address of the image.

Figure 22:
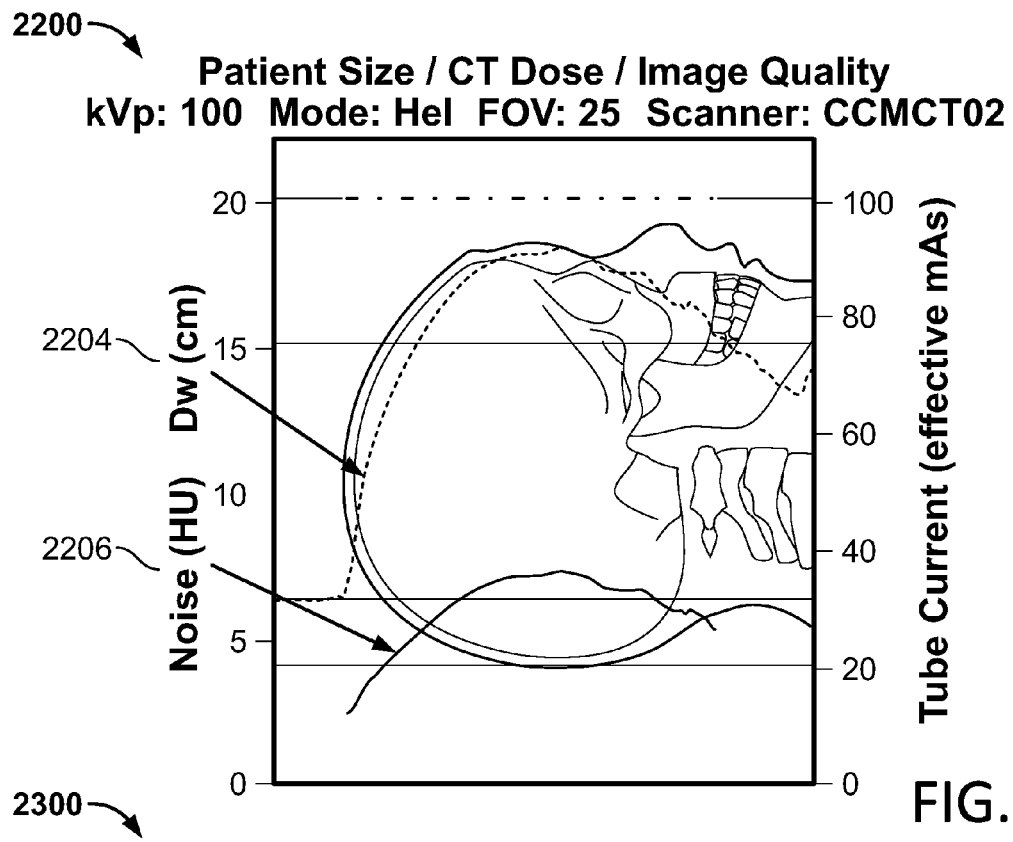
FIG. 22 shows a lateral head topogram with $D_W$ and Noise mapped.
Figure 23:
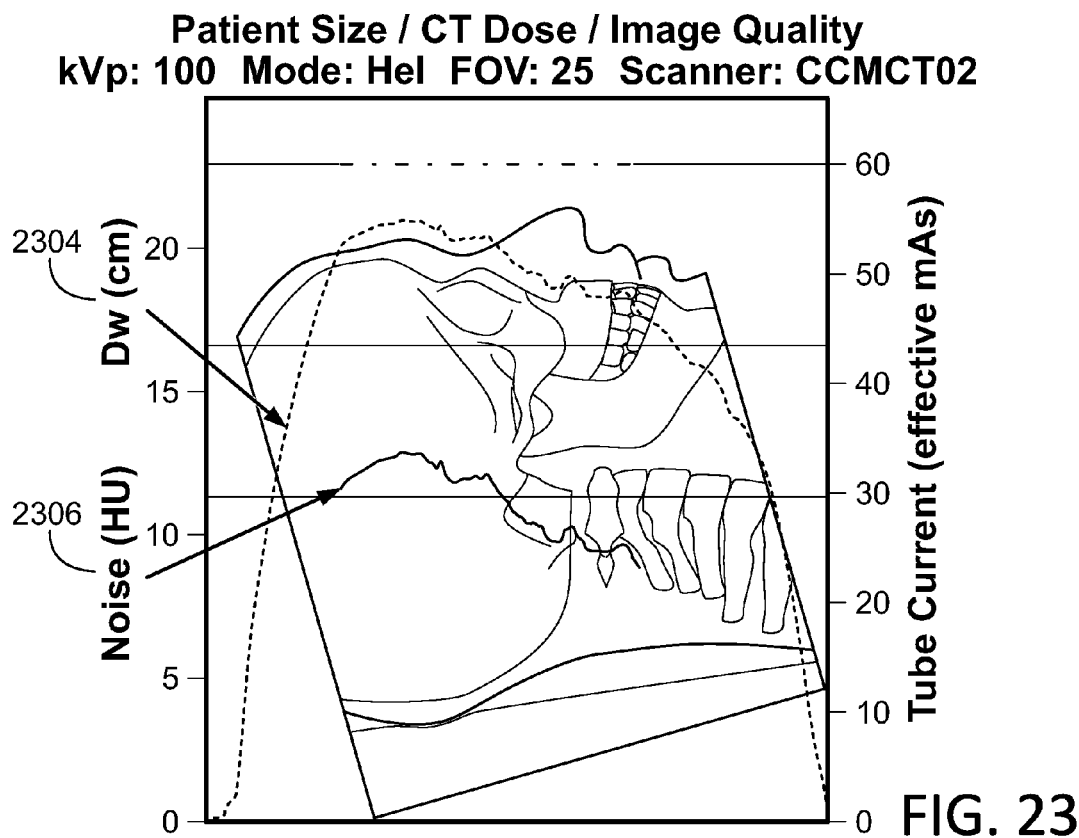
FIG. 23 shows a rotated lateral head topogram.

FIG. 22 shows an example lateral head topogram 2200. For cases where only a lateral topogram is available, the application performs the calculations and maps the results 2204 and 2206 to the lateral topogram such as the one shown in FIG. 22, with some exceptions. First, because the table is not present on the lateral image, the application does not subtract out the background attenuation from the table. The constants used for these studies are derived from phantom noise measurements obtained without the table. Thus, patient size is represented by $D_W$ rather than $D_{W\_net}$. Second, for head and facial CTs, the gantry is often tilted to acquire the images in a plane parallel to the planum sphenoidale. FIG. 23 shows rotating the lateral head topogram 2300 by mapping size, dose, and quality data. The processor compensates for this by first rotating the image 2300 by the corresponding angle and then mapping the size 2304, dose, and image quality data 2306, shown in FIG. 23.

Because some studies entail more than one scan, or "radiation event," in the same study (e.g. noncontrast and postcontrast phase CT of the abdomen for evaluation of a liver mass in a single study), the above calculations are performed for each radiation event. The processor is able to differentiate radiation events by looking up the scan date and time in the DICOM header information.

Data Storage

The exemplary processor calculates overall statistics for each study, including the minimums, means, and maximums of the following parameters: mA, mAs, $D_W$, $D_{W\_net}$, $CTDI_{vol}$, DLP, SSDE, and noise. The processor also looks up other pertinent data from the DICOM header information, including patient name, accession number, medical record number, date of birth, date of the examination, scanner, medical center, examination name, etc.

In an exemplary embodiment, these data are sent to corresponding fields in the database, hereafter referred to as the Guidance database. The topogram, with superimposed graphs of patient size, effective mAs, and image noise data, is also sent to the database. This relational database contains tables for records that are unique for the study, the series (i.e. a single radiation event), and the instance (a single axial slice). These records are linked with unique identifiers in each table.

The exemplary processor assesses the $CTDI_{vol}$ for each slice based on the scan mode, kV, mA, exposure time, pitch factor, and focal spot size. The mean $CTDI_{vol}$ ($CTDI_{vol\_mean}$) is calculated for the study by averaging the $CTDI_{vol}$ for each slice. The dose-length product (DLP), the product of the $CTDI_{vol}$ and the length of the scan, is also calculated for the study based on the calculated $CTDI_{vol}$ for each slice. The mean SSDE is calculated for the study by averaging the SSDE for each slice.

In an exemplary embodiment, all equations for patient size calculations, image noise and radiation estimates, and target image noise assessments described above are contained in and utilized by the processor.

Data Analysis Display and Monitoring

Figure 25:
FIG. 25 shows a screen capture image of the study analysis, including a search page.

FIG. 24 and FIG. 25 shows a screen capture image 2400 and 2500 of the exemplary study analysis application. Based on the Guidance database, the study analysis application is used to enable the analysis of the studies both individually and collectively. The application contains a search page, enabling the search for an individual study or a query for a collection of studies.

Figure 26:
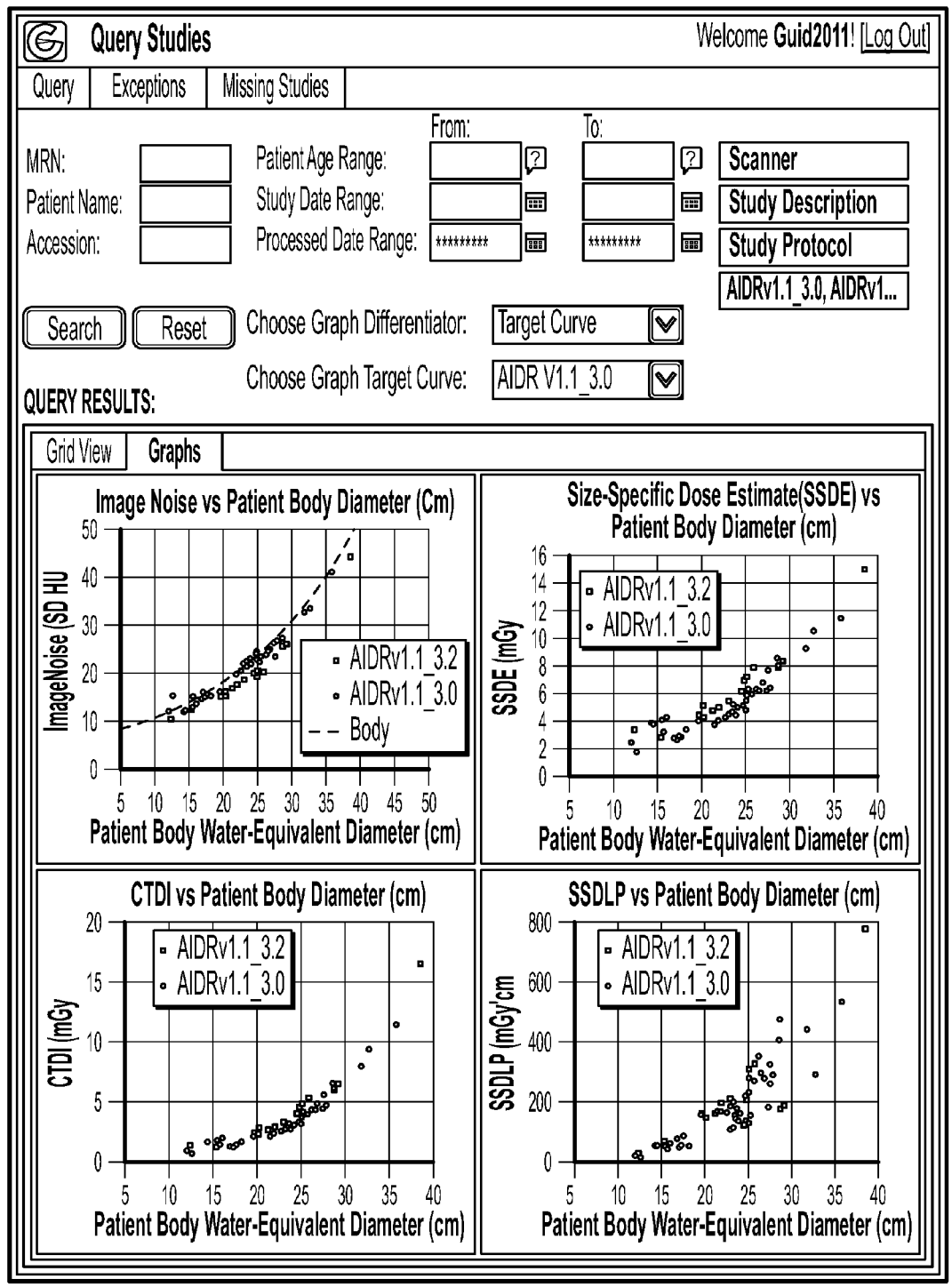
FIG. 26 shows a screen capture of display charts of study data compared to patient $D_W$.

Instead of selecting an individual study, the user can choose to display charts 2600 related to the queried cases, shown in FIG. 26. This displays charts of study data compared to patient $D_W$, such as mean image noise, $CTDI_{vol}$, DLP, and SSDE. The study that are graphed are the same as those in the query page; the user can toggle back and forth between the two views. Therefore, the user can filter the data shown in the graph by changing the query search and filter parameters. A target curve that the user selects can be mapped to the image noise graph. Data points on each graph can be differentiated by color according to the selected criteria. Selection of one of the points launches the study analysis page for that study.

Figure 27:
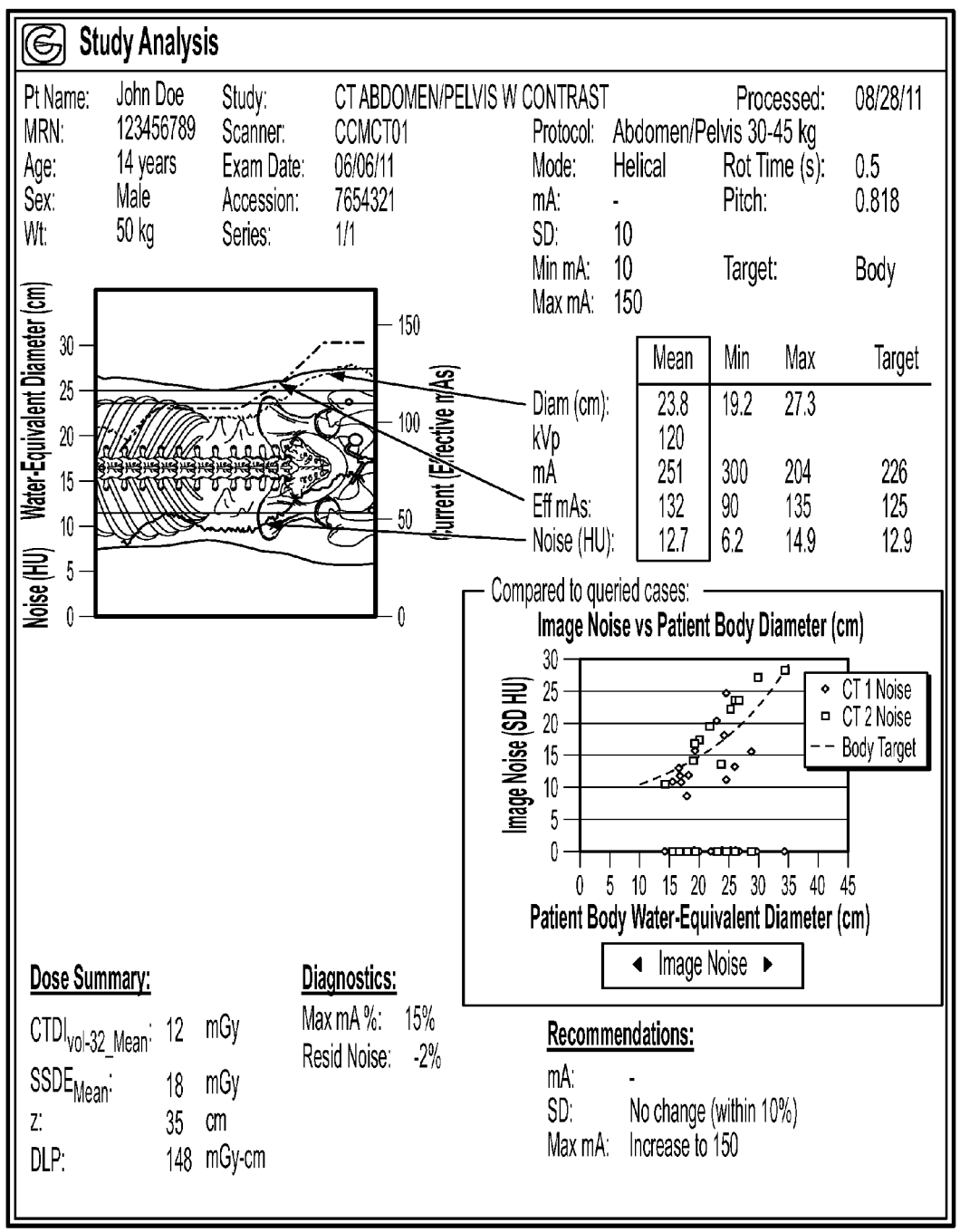
FIG. 27 shows an example selection of an individual study.
Figure 28:
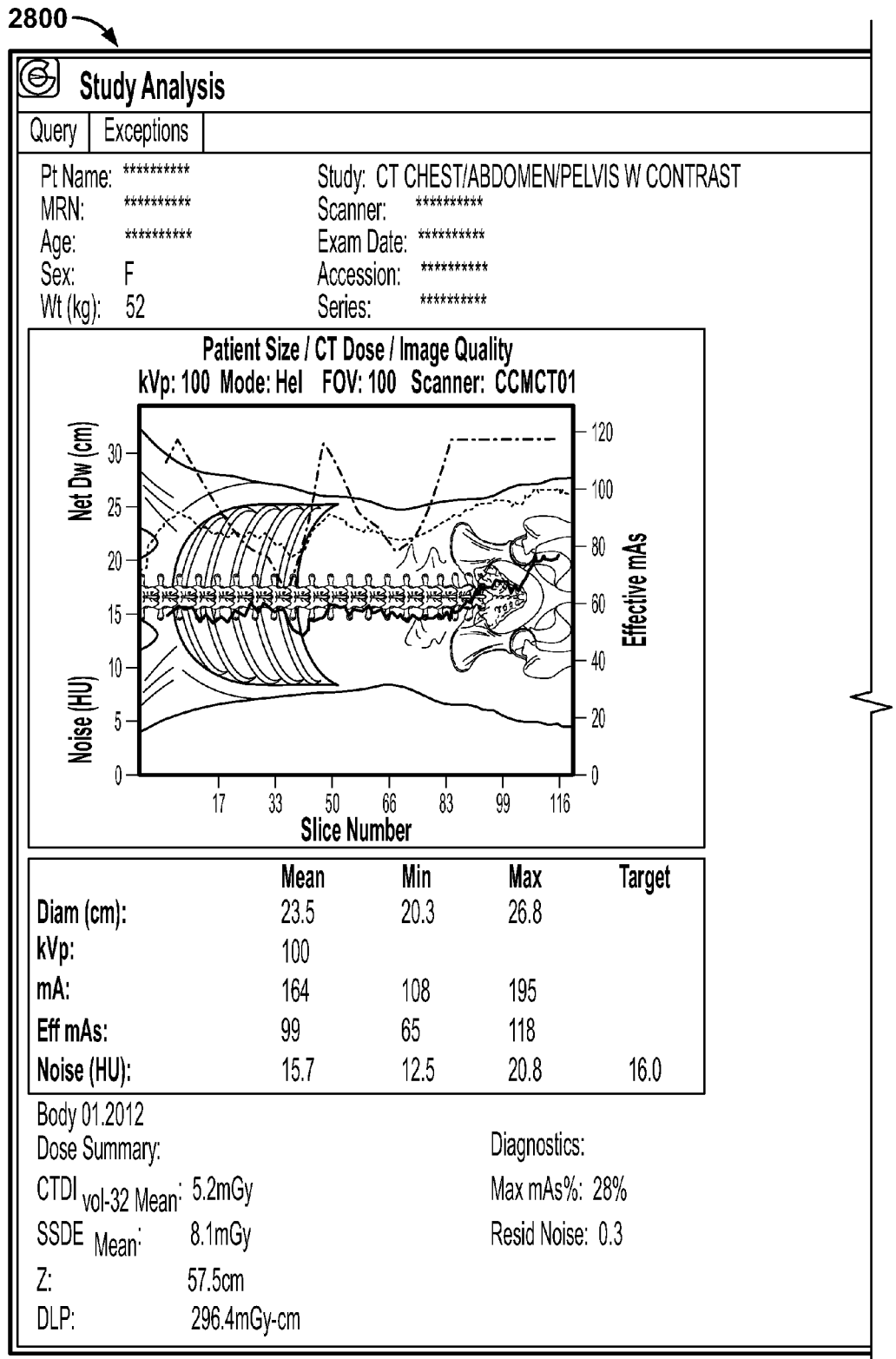
FIG. 28 shows a screen capture of a compilation of pertinent information for a given study.
Figure 28:
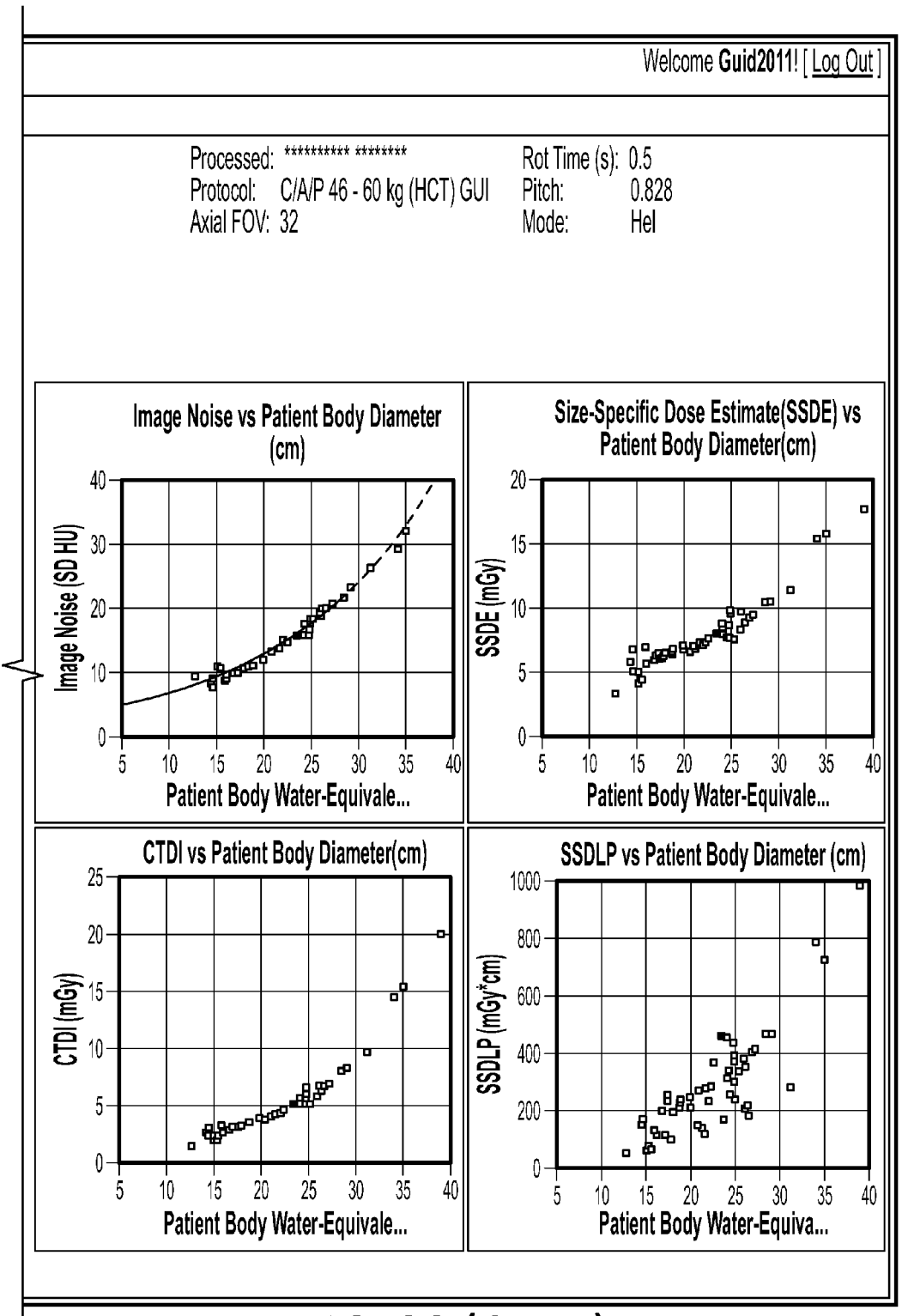

The selection of an individual study from the search page launches the study analysis page shown in FIG. 27 and FIG. 28 which displays all of the pertinent information 2700 and 2800 of a given study, including patient demographic data, study acquisition information, calculated image quality and dose values, and the mapped topogram image. In FIG. 27, screen shot 2700 displays the target noise, as well as the mA and effective mAs that would result in the target noise, calculated by the application and included in the study analysis page. Based on these parameters, the application calculates the residual noise (target image noise divided by actual image noise). The application also assesses whether a change in the mA, SD setting, or maximum mA is warranted.

In FIG. 28, screen shot 2800 displays the target noise calculated by the application and included in the study analysis page. Based on these parameters, the application calculates the residual noise (actual image noise minus target image noise).

The study analysis page also displays the mean study image noise and dose information graphically. Other studies that were included in the search are also plotted on the same graphs for comparison. The selected target image noise curve may also be superimposed on the image noise curve. In this manner, the user can determine how well the actual image noise from the selected study matched the target image noise, and how it compares to other studies of the same type.

Monitoring and Reporting

The exemplary processor application allows the user to set limits on image noise data, as a function of patient size, as desired for each protocol or study type. When the difference between the actual average study image noise and target image noise exceeds these limits, the exemplary processor application automatically sends an email to designated recipients informing them that a study has been performed in which the average noise was outside of the expected range.

Data from a query can be exported into an external data file. This file includes all study data in the database, not only those that are displayed by the study analysis application. These data can be used for research, internal monitoring, or reporting. The data can be deidentified and transmitted to both internal and external reviewers or reviewing organizations, such as a national data registry or regulatory agency. With the cooperation of such an organization, an automatic report can be developed and periodically transmitted to the organization.

Protocol Centralization.

Figure 29:
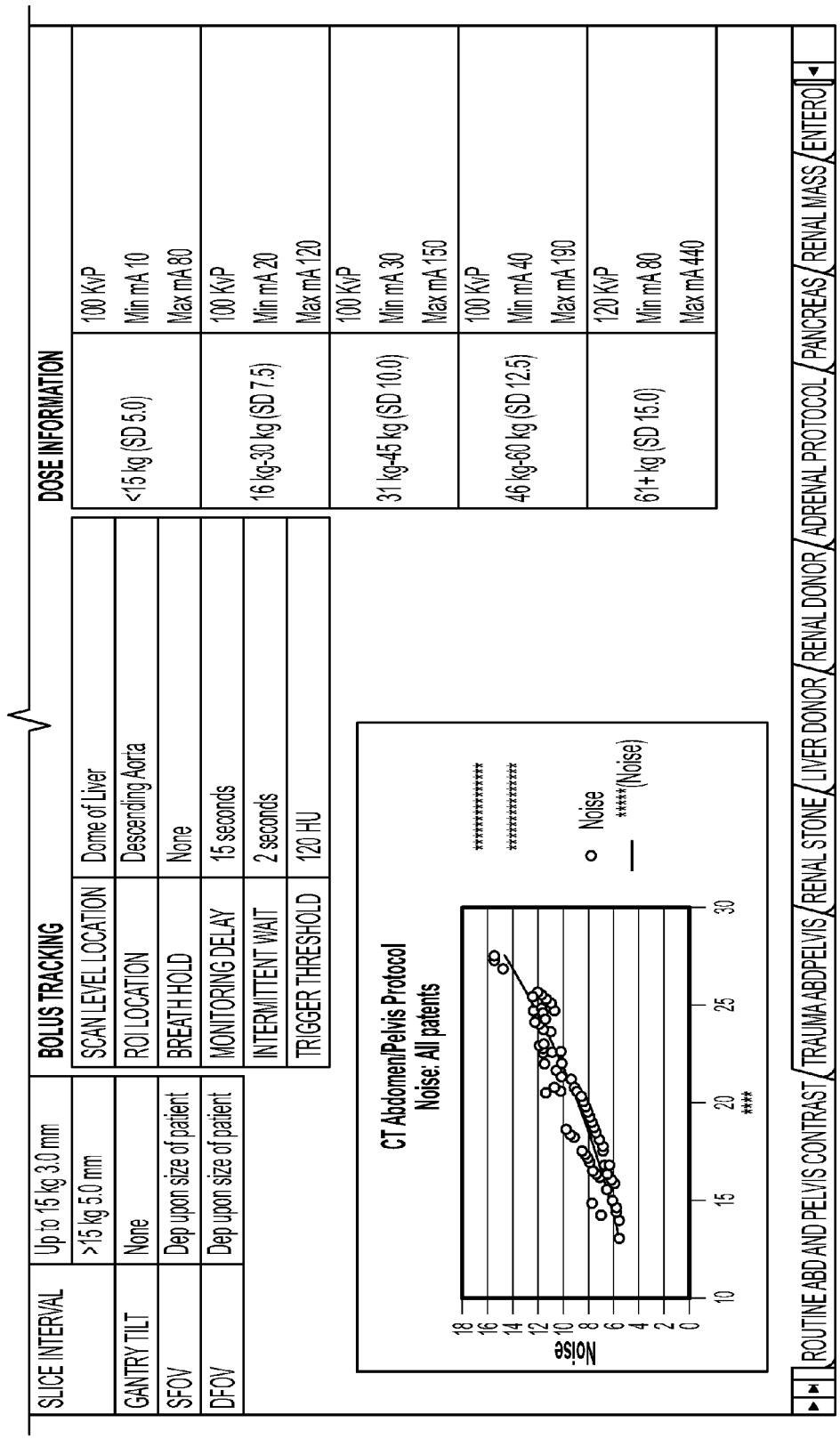
FIG. 29 shows details of parameters of an example CT scan.

The system may maintain all scan protocols for all scanners for a given enterprise within a single database, with the capability of interfacing with all scanners in a given organization to update protocol changes for all scanners. The system may contain a database that contains information regarding the protocols for each CT scanner within the organization. Thus, if an organization chooses, all CT scan protocols for all scanners controlled by the organization, whether it be at one or many hospitals, can be centralized into one location. FIG. 29 shows relevant CT scan parameters 2900, including mA, kV, pitch, scan length, contained within the database for each CT scanner within the organization All relevant CT scan parameters, including mA, kV, pitch, scan length, etc, are contained within the database. Patient criteria are also contained within the database, including age or weight parameters. Special instructions for the CT technologist are also contained within the database. Therefore, this database becomes a central repository for all CT protocols throughout the organization.

Aggregate data corresponding to each protocol may be linked to the protocol form in the database. Thus, when the protocol is displayed, the aggregate data corresponding to that protocol is displayed as well, shown in screen shot 2900. The system may also be capable of predicting image quality and dose performance for a protocol either based on historical data in the system or a data file of representative patients provided to the institution. Thus, protocol changes can be simulated and its influence on dose and image quality can be predicted.

System Automation

Figure 30:
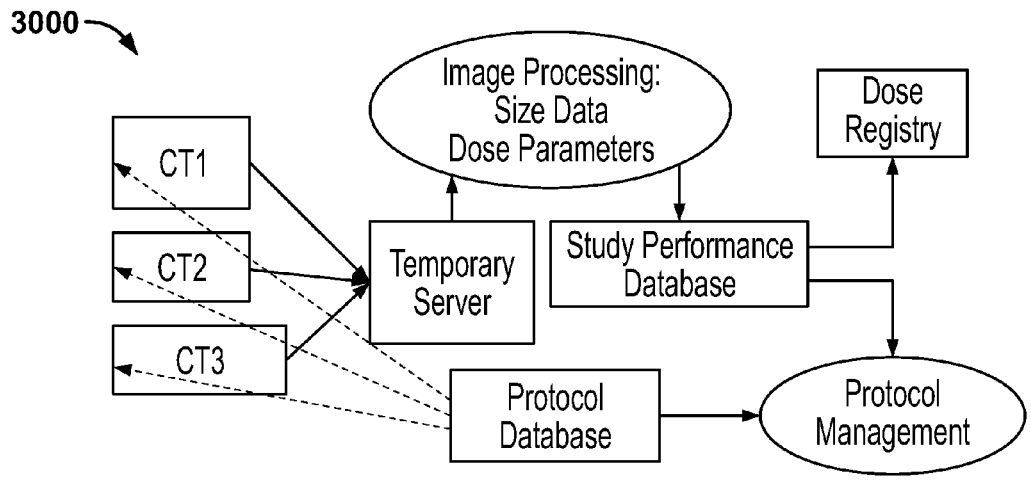
FIG. 30 is a block diagram for the system.
Figure 31:
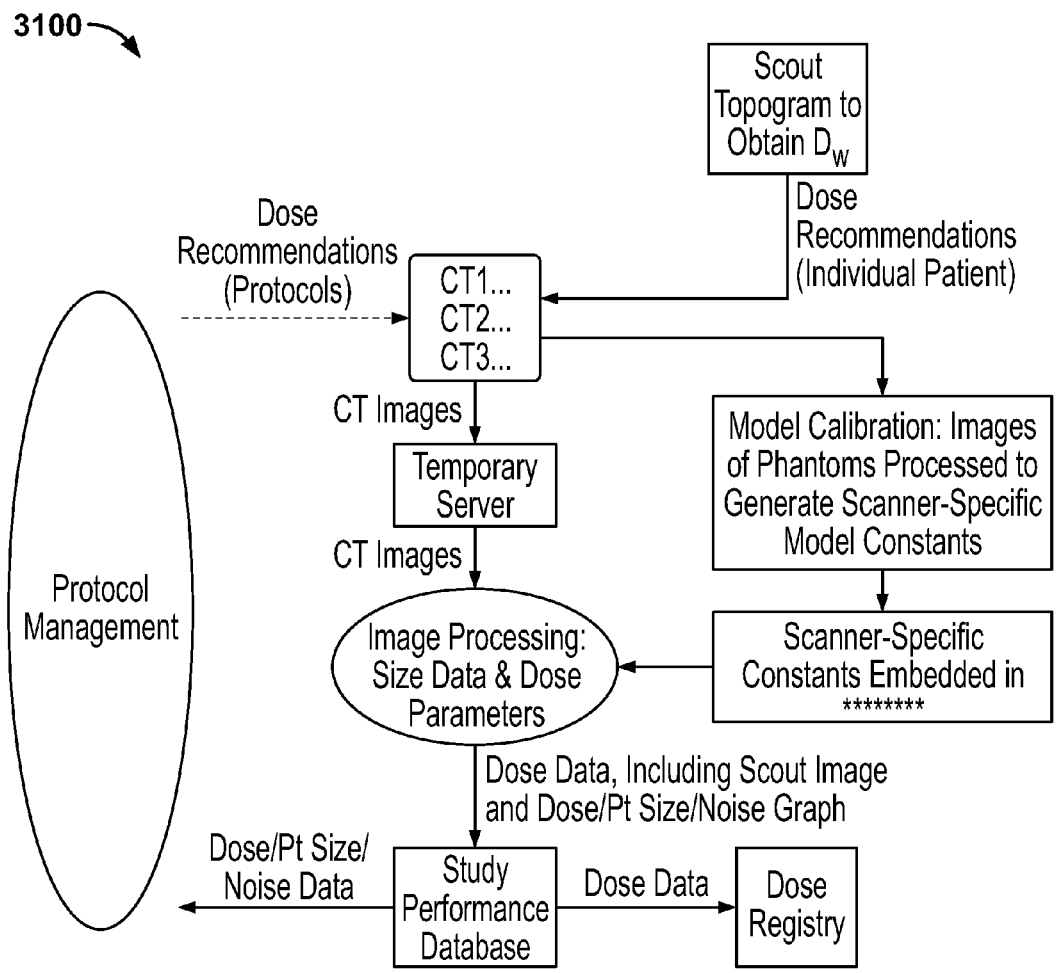
FIG. 31 is an alternate block diagram for the system.

FIG. 30 and FIG. 31 show block diagrams 3000 and 3100 for the system. An exemplary system uses a software application to automatically process images using the above calculations. A script is in place to automatically send images to an independent temporary server from the CT scanner or from the Picture Archiving and Communication System (PACS). All images from a study are sent to that study's unique folder on the temporary server. The image processing application processes the images on a periodic basis, determined by the user.

An exemplary system automates image processing, data storage, analysis, display, monitoring, and reporting.

An exemplary environment for implementing various aspects of the invention may include one or more computers that may be installed within, or operatively associated with, a CT scanning system, or may run completely separate from the CT scanning system. The computer may include a processing unit, a system memory and a system bus. The computer's system bus couples system components including, but not limited to, the system memory to the processing unit. The processing unit may be any of various commercially available processors. Dual microprocessors and other multi processor architectures may also be employed as the processing unit.

The system bus may be any of several types of bus structure that may further interconnect to a memory bus (with or without a memory controller), a peripheral bus, and a local bus using any of a variety of commercially available bus architectures. The system memory may include read only memory (ROM) and/or random access memory (RAM). A basic input/output system (BIOS) is stored in a nonvolatile memory such as ROM, EPROM, EEPROM, which BIOS contains the basic routines that help to transfer information between elements within the computer, such as during start-up. The RAM may also include a high-speed RAM such as static RAM for caching data.

The computer may further include an internal hard disk drive (HDD) (e.g., EIDE, SATA), which internal hard disk drive may also be configured for external use in a suitable chassis, a magnetic floppy disk drive (FDD), (e.g., to read from or write to a removable diskette) and an optical disk drive, (e.g., reading a CD-ROM disk or, to read from or write to other high capacity optical media such as the DVD). The hard disk drive, magnetic disk drive and optical disk drive may be connected to the system bus by a hard disk drive interface, a magnetic disk drive interface and an optical drive interface, respectively. The interface for external drive implementations includes at least one or both of Universal Serial Bus (USB) and IEEE 1394 interface technologies.

The drives and their associated computer-readable media may provide nonvolatile storage of data, data structures, computer-executable instructions, and so forth. For the computer, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules may be stored in the drives and RAM, including an operating system, one or more application programs, other program modules and program data. All or portions of the operating system, applications, modules, and/or data may also be cached in the RAM. It is appreciated that the invention may be implemented with various commercially available operating systems or combinations of operating systems.

It is within the scope of the disclosure that a user may enter commands and information into the computer through one or more wired/wireless input devices, for example, a touch screen display, a keyboard and/or a pointing device, such as a mouse. Other input devices may include a microphone (functioning in association with appropriate language processing/recognition software as know to those of ordinary skill in the technology), an IR remote control, a joystick, a game pad, a stylus pen, or the like. These and other input devices are often connected to the processing unit through an input device interface that is coupled to the system bus, but may be connected by other interfaces, such as a parallel port, an IEEE 1394 serial port, a game port, a USB port, an IR interface, etc.

A display monitor or other type of display device may also be connected to the system bus via an interface, such as a video adapter. In addition to the monitor, a computer may include other peripheral output devices, such as speakers, printers, etc.

The computer may operate in a networked environment using logical connections via wired and/or wireless communications to one or more remote computers. The remote computer(s) may be a workstation, a server computer, a router, a personal computer, a portable computer, a personal digital assistant, a cellular device, a microprocessor-based entertainment appliance, a peer device or other common network node, and may include many or all of the elements described relative to the computer. The logical connections depicted include wired/wireless connectivity to a local area network (LAN) and/or larger networks, for example, a wide area network (WAN). Such LAN and WAN networking environments are commonplace in offices, and companies, and facilitate enterprise-wide computer networks, such as intranets, all of which may connect to a global communications network such as the Internet.

The computer may be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi (such as IEEE 802.11x (a, b, g, n, etc.)) and Bluetooth™ wireless technologies. Thus, the communication may be a predefined structure as with a conventional network or simply an ad hoc communication between at least two devices.

The system may also include one or more server(s). The server(s) may also be hardware and/or software (e.g., threads, processes, computing devices). The servers may house threads to perform transformations by employing aspects of the invention, for example. One possible communication between a client and a server may be in the form of a data packet adapted to be transmitted between two or more computer processes. The data packet may include a cookie and/or associated contextual information, for example. The system may include a communication framework (e.g., a global communication network such as the Internet) that may be employed to facilitate communications between the client(s) and the server(s).

Scanner-Specific Derivation of Model Constants

Figure 32:
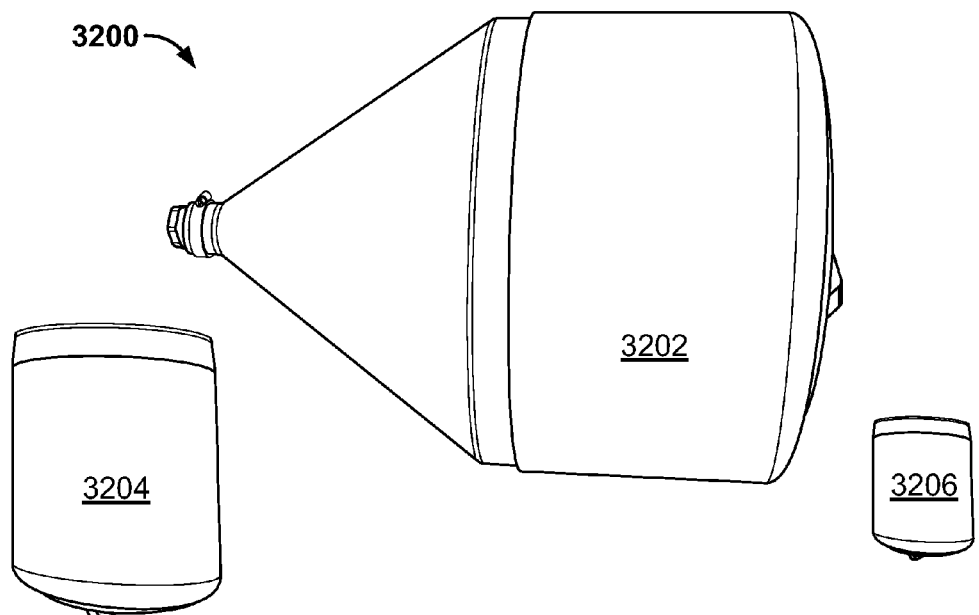
FIG. 32 depicts three water phantoms of varying size.
Figure 33:
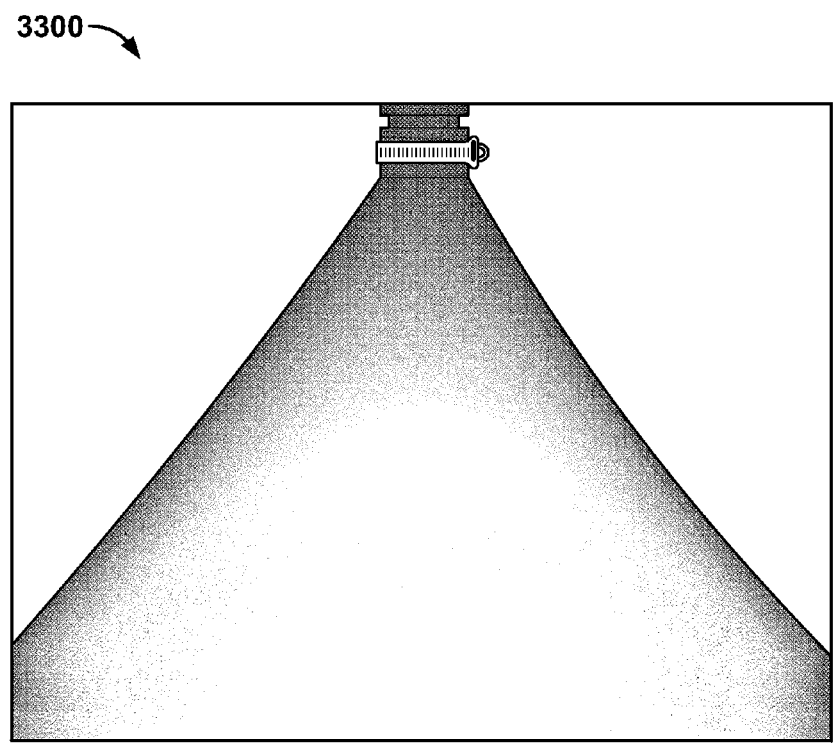
FIG. 33 shows a topogram of a conical water phantom.
Figure 34:
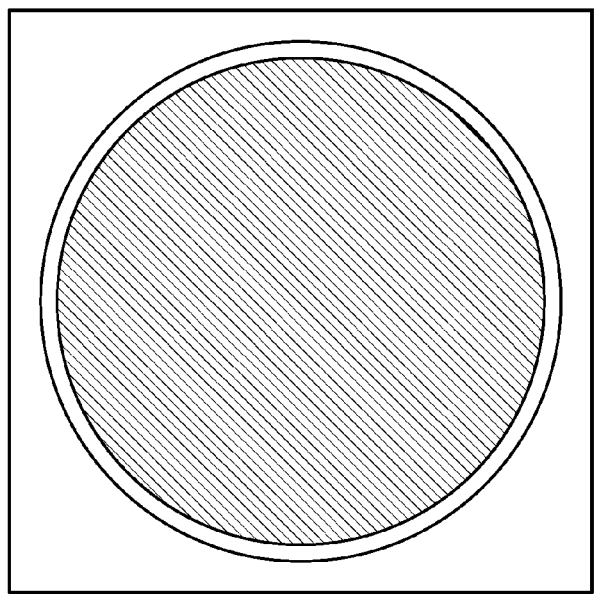
FIG. 34 shows image noise as the standard deviation of the CT units.
Figure 35:
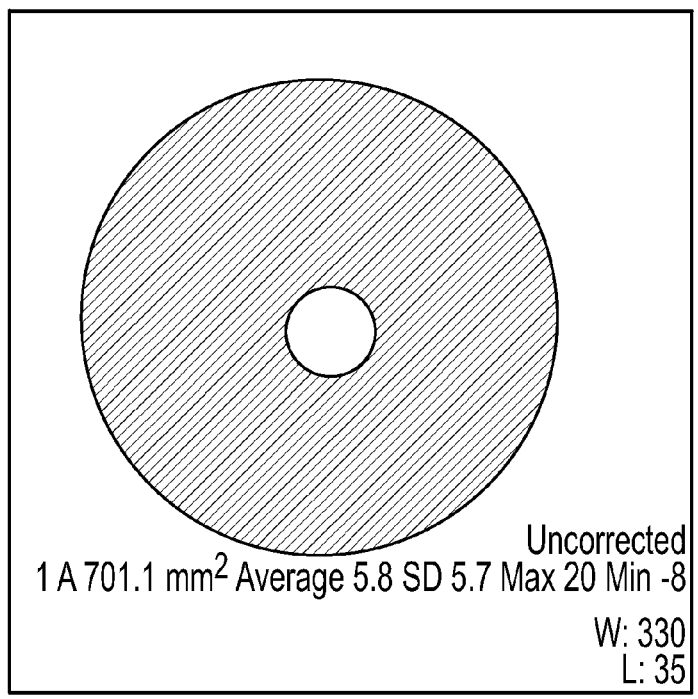
FIG. 35 shows an axial slice of a conical water phantom.

FIG. 32 depicts three water phantoms 3200 of varying size. In order to assess the performance of each scanner at relevant settings such as mode, kV, data collection diameter, and mAs, test scans may be performed on a conical phantom 3202 with a diameter range of approximately 5 cm to 50 cm as pictured in FIG. 32. Phantoms may also be ellipsoid 3204 phantoms or anthropomorphic 3206 adult or child phantoms. Axial scans may be performed with the scanner in each relevant mode with the phantom on the table as well as with the phantom off of the table. Examples of the topogram 3300 and axial image 3400 from these scans are shown in FIG. 33 and FIG. 34, respectively. FIG. 35 shows image noise is defined as the standard deviation of the CT units within a 3 cm diameter circle at the center of the imaged water phantom 3500.

In an embodiment, to avoid having to manually measure the noise from each image, a software application (calibrator) opens the image files and processes them image by image. For each axial image 800, the calibrator creates a mask that defines the boundary between the area of the image that defines the phantom compared to the surrounding air. The calibrator determines the effective diameter of this shape (which is the $D_W$) and finds the centroid. The calibrator creates a 3 cm diameter circle centered at the centroid and calculates the standard deviation of this region, shown above FIG. 8.

The topogram image may be converted to a data matrix. A row-by-row integration of the DU multiplied by the pixel height is performed to provide $DU_{sum}$ for each row. The calibrator application exports all of these data points into a single data file, including the topogram data matrix, $DU_{sum}$, the $D_W$, the noise for each image, and scan parameters and settings.

The data file may then be processed by another application, the model generator, which organizes the data and plots them 900 as shown in FIG. 9. For each point, the model generator may calculate the expected image noise based on the noise equation shown above, beginning with dummy constants. The error between each point and the model is calculated, and all of the errors are summed. The model generator performs a solver routine, minimizing the error sum by changing the constants, $c_0$, $c_1$, $c_2$, $c_3$, $c_4$, and $c_{me}$, resulting in the plot 1000 in FIG. 10. This may be performed for each setting.

In an embodiment, the summed errors for each setting are summed as a global error sum. All settings are based on one set of $c_0$, $c_1$, $c_2$, $c_3$, $c_4$, and $c_{me}$, with each setting containing a $c_0$ and $c_{me}$ correction factor, as previously described. A solver routine is performed again for all settings simultaneously, minimizing the global error sum by changing the model set constants $c_0$, $c_1$, $c_2$, $c_3$, $c_4$, and $c_{me}$, and each setting's correction factors, $c_0$ and $c_{ee}$, simultaneously producing dose/noise plots 1000 and 1100 in FIG. 10 and FIG. 11.

In an embodiment, the model generator also finds the $c_{scout}$ for each setting by correlating the $DU_{sum}$ with the known phantom diameter, as described above.

Following from the above description and invention summaries, it should be apparent to those of ordinary skill in the art that, while the methods and apparatuses herein described constitute exemplary embodiments of the present inventions, it is to be understood that the inventions contained herein are not limited to the above precise embodiment and that changes may be made without departing from the scope of the inventions. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A computed tomography (CT) scanner, comprising:
an x-ray source;
an x-ray detector; and
a computer system operatively coupled to the x-ray source and x-ray detector, and configured to perform the steps of:
obtaining a patient size data;
establishing a target noise equation, the target noise equation being a function of the patient size data; and
applying the target noise equation against a measured noise equation, the measured noise equation being a function of the patient size data, to derive CT scan parameters for a given CT scan.

2. The computed tomography scanner of claim 1, wherein;
   the step of applying the target noise equation against a measured noise equation to derive CT scan parameters for a given CT scan includes a step of setting the target noise equation equal to measured noise equation for the patient size data, and solving for a radiation dose parameter.

3. The computed tomography scanner of claim 2, wherein the radiation dose parameter includes mAs.

4. The computed tomography scanner of claim 3, wherein the target noise equation is $$\text{Target noise} = c_T + a_T e^{b_T D_W}$$

where $c_T$, $a_T$, and $b_T$ are empirically-derived constants and where $D_W$ is patent size data.

5. The computed tomography scanner of claim 1, where patient size data is one of: patient weight, and patient water-equivalent diameter.

6. The computed tomography scanner of claim 4, wherein the measured noise equation is $$\text{Noise} = c_0 + c_c (c_{em} \cdot em)^{r_c} \cdot e^{[c_r (c_{em} \cdot em)^{r_r} \cdot D_W]}$$

where $c_0$, $c_c$, $r_c$, $c_r$, $r_r$, and $c_{em}$ are empirically-derived constants and em is effective mAs.

7. The computed tomography scanner of claim 4, wherein the measured noise equation is:

$$\sigma = c_0 + c_1 (c_{m_e} m_e)^{c_2} e^{[D_W c_3 (c_{m_e} m_e)^{c_4}]}$$

where $\sigma$ is image noise, $m_e$ is effective mAs, $D_W$ is the patient's water-equivalent diameter, and $c_0$, $c_1$, $c_2$, $c_3$, $c_4$, and $c_{me}$ are constants.

8. The computed tomography scanner of claim 2, wherein the step of solving for the radiation dose parameter is an iterative process.

9. The computed tomography scanner of claim 1, wherein the target noise equation is established based, at least in part, upon one or more radiologist's subjective assessments of appropriate image quality.

10. The computed tomography scanner of claim 1, wherein:
    the measured noise equation is a dose modulation noise equation;
    the step of applying the target noise equation against the measured noise equation to derive CT scan parameters for a given CT scan includes a step of setting the target noise equation equal to dose modulation noise equation for the patient size data, and solving for a radiation dose parameter.

11. The computed tomography scanner of claim 10, wherein the dose modulation noise equation is, $$\text{Noise} = c_0 + c_c (c_{SD} \cdot SD)^{r_c} \cdot e^{[c_r (c_{SD} \cdot SD)^{r_r} \cdot D_W]}$$

where $c_0$, $c_c$, $r_c$, $c_r$, $r_r$, and $c_{SD}$ are empirically-derived constants and where $D_W$ is the patient size according to water-equivalent diameter; and
where the radiation dose parameter is a target noise parameter SD.

12. The computed tomography scanner of claim 1, wherein the measured noise equation is derived by scanning and measuring noise data of a water phantom.

13. The computed tomography scanner of claim 12, wherein the water phantom is one of: a conical water phantom, an anthropomorphic water phantom, and an ellipsoid phantom.

14. The computed tomography scanner of claim 1, wherein the target noise equation and measured noise equation are selected from a respective group of equations stored in the computer system, the selection being based upon a desired CT application.

15. The computed tomography scanner of claim 14, wherein the group of equations include equations for one or more of the following CT applications:
    a body target application;
    a lung target application; and
    a bone target application.

16. The computed tomography scanner of claim 1, wherein the patent size data is a mean value of water-equivalent diameter taken for the patient over a scan axis.

17. The computed tomography scanner of claim 16, wherein the mean value of water-equivalent diameter is derived by performing a row-by-row integration of topogram image data for each cross-sectional level along the scan axis.

18. The computed tomography scanner of claim 1, wherein the CT scan parameters include one or more of kV, mAs and dose modulation settings.

19. The computed tomography scanner of claim 1, further comprising a step of performing a CT scan utilizing one or more of the derived CT scan parameters.

20. The computed tomography scanner of claim 19, further comprising a step of storing the derived CT scan parameters and the patient size data to the computer system in a database record associated with the CT scan for subsequent data analysis.

21. The computed tomography scanner of claim 1, further comprising a step of signalling to an output operatively connected to the computerized system if one or more of the derived CT scan parameters fall outside of a set of selected CT scan parameters.

22. A computed tomography system, comprising:
    a processor;
    a protocol manager;
    a dose registry;
    a database in communication with the system; and
    a scanner in communication with the processor capable of scout scanning and CT tomography scanning;
    wherein the protocol manager is configured to perform the steps of:
        receive patient size data;
        establish a target image quality parameter for the scan at least partially based on the received patient size data, wherein the target image quality parameter is based at least in part on a target visual noise parameter established by determining where a dose modulation noise curve is equal to a target noise curve;
        retrieve scanner parameter information from the database;
        determine a scan protocol based on the target image quality parameter and the scanner parameter information;
        recommend the determined scan protocol;
        scan the patient utilizing a radiation dose based on the determined scan protocol;

display the scan image to a display operatively connected to the system;
measure the scan image for noise information; and
update the database with at least one of the measured noise information, the determined scan protocol, the scan image, and the radiation dose.

23. The system of claim 22, wherein determining the scan protocol includes determining a size specific radiation dose estimate (SSDE).

24. The system of claim 23, wherein the radiation dose is based, at least in part, upon the determined SSDE.

25. The system of claim 22, wherein determining the scan protocol includes determining one or more scanner settings.

26. The system of claim 22, wherein the step of scanning the patient includes setting the scanner at the determined scanner settings.

27. The system of claim 22, further including the protocol manager being configured to perform the step of: process water phantom images to yield scanner parameters by scanning a water phantom and saving an image noise information and scanner parameters to the database.

28. The system of claim 23, wherein, the step of scanning the patient includes administering the determined SSDE to the patient.

29. The system of claim 22, further including the protocol manager being configured to perform the step of: determine scanner parameters based on the target image quality parameters.

30. The system of claim 22, wherein the estimate of patient size data is based upon scanning a patient with a scout scan on the scanner, and creating a topogram with the scout scan.

31. The system of claim 30, further including the protocol manager being configured to perform the step of:
perform a row-by-row integration of the topogram by the scanner to determine water equivalent diameter for a slice ($D_{W\_net}$) for each cross-sectional level along the z-axis; and
map $D_{W\_net}$ to the topogram.

32. The system of claim 31, further comprising the protocol manager is configured to perform the steps of: calculate the estimated noise calculated at each slice and map the estimated noise to the topogram.

33. The system of claim 22, wherein the estimate of the patent size is based upon:
scanning the patient with a scout scan to acquire the patient's thickness $T_w$; and
using $T_w$ to cross-reference a corresponding patient size expressed as a water equivalent diameter $D_W$ from the database.

34. The system of claim 23, wherein updating the database includes aggregating the parameters in the database with at least one of:
the SSDE information, the noise information, the scanner parameters, and patient size.

35. The system of claim 22, wherein the scanner parameters includes one or more scanner constants and one or more scanner performance data.

36. The system of claim 35, further including the protocol manager being configured to perform the steps of:
derive scanner parameters by performing at least one water phantom scan with the scanner, with at least one scanner setting and one scanner mode;
measure the image noise;
solve for a chosen constant with an appropriate equation; and
save the settings parameters and image noise to the database.

37. The system of claim 36, wherein the scanner characteristics are derived by scanning the water phantom and measuring the noise values, wherein the water phantom is one of: on a table, and off a table.

38. The system of claim 36, wherein the water phantom is a water filled object.

39. The system of claim 38, wherein the water phantom is one of: a conical water phantom, an anthropomorphic water phantom, and an ellipsoid water phantom.

40. The system of claim 38, wherein the water phantom is a conical phantom having a diameter range of about 5 cm to 50 cm.

41. The system of claim 22, wherein the scanner parameters include, for at least one mode and one setting, at least one of:
$c_{scout}$; magnification factor (m.f.); target noise constants $c_T$, $a_T$, and $b_T$; noise constants $c_0$, $c_c$, $r_c$, $c_r$, $r_r$, and $c_{em}$; a, b; contrast sensitivity; and special resolution; and
a dose kV, mA, mAs; a dose $CTDI_{vol}$; a ratio of $CTDI_{vol}$ to effective mAs; dose length product (DLP).

42. The system of claim 41, wherein scanner settings include at least one of: voltage potential, bowtie filter, focal spot size.

43. The system of claim 41, further comprising the protocol manager is configured to perform the steps of:
derive a parameter $c_{scout}$ for the scanner by scanning the water phantom with a known thickness $T_W$,
solve for $c_{scout}$ where $T_W = c_{scout} DU$, where DU is density units, and save $c_{scout}$ to the database; and
use the constant $c_{scout}$ to determine a patient size by water equivalent diameter $D_W$, where $$D_W = 2 \cdot c_{scout} \sqrt{\frac{DU_{sum}}{\pi}}.$$

44. The system of claim 41, wherein $c_T$, $a_T$, and $b_T$ are derived by:
scanning a water phantom having a diameter $D_w$ with the scanner;
measuring the noise from the water phantom scan;
solving for the equation Target noise=$c_T + a_T \cdot e^{b_T \cdot D_W}$; and transmitting the values of $c_T$, $a_T$, and $b_T$ to the database.

45. The system of claim 41, wherein constants $c_0$, $c_c$, $r_c$, $c_r$, $r_r$, and $c_{em}$ are derived by:
scanning a water phantom having diameter $D_w$ with the scanner;
measuring the noise from the water phantom scan;
solving for the equation Noise = $c_0 + c_c(c_{SD} \cdot SD)^{r_c} \cdot e^{[c_r(c_{SD} \cdot SD)^{r_r} \cdot D_W]}$;

and
transmitting the values of $D_w$, $c_0$, $c_c$, $r_c$, $c_r$, $r_r$, and $c_{em}$ to the database.

46. The system of claim 22, further including the protocol manager being configured to perform the step of:
show graphically a measure of CT image quality for the scan on the display.

47. The system of claim 22, wherein the dose modulation noise curve is modeled according to the following equation:

$$\text{Noise} = c_0 + c_c (c_{SD} \cdot SD)^{r_c} \cdot e^{[c_r(c_{SD} \cdot SD)^{r_r} \cdot D_W]}$$

and the constants $c_0$, $c_c$, $r_c$, $c_r$, $r_r$, and $c_{em}$ are aggregated scanner parameters in the database, $D_W$ is the patient size expressed as patient's water-equivalent diameter, and wherein SD a variable target noise scanner setting.

48. The system of claim 22, wherein the measured noise equation is:

$$\sigma = c_0 + c_1 (c_{m_e} m_e)^{c_2} e^{[D_W c_3 (c_{m_e} m_e)^{c_4}]}$$

where $\sigma$ is image noise, $m_e$ is effective mAs, $D_W$ is the patient size expressed as patient's water-equivalent diameter, and $c_0$, $c_1$, $c_2$, $c_3$, $c_4$, and $c_{me}$ are constants.

49. The system of claim 22, wherein the target image noise curve is established according to the equation:

$$\text{Target noise} = c_T + a_T e^{b_T D_W}$$

wherein $c_T$, $a_T$, and $b_T$ are scanner parameter constants found in the database, and $D_W$ is patient size according to a water equivalent diameter.

50. The system of claim 22, further including the protocol manager being configured to perform the step of:
provide one or more recommended scan parameters to an operator according to the target image curve.

51. The system of claim 23 wherein the step of determining the SSDE, includes using the patient size expressed as a water equivalent diameter $D_w$ and solving for the equation: $SSDE = (a \cdot e^{-b \cdot D_W}) CTDI_{vol}$.

52. The system of claim 51, further including the protocol manager being configured to perform the step of: calculate a dose-length product (DLP), wherein the DLP is the product of the $CTDI_{vol}$ and the length of the scan, based on the calculated $CTDI_{vol}$ for each slice n, and saving the DLP to the database.

53. The system of claim 22, further including the protocol manager being configured to perform the steps of:
calculate statistics for a study including the minimum, mean, and maximum for one or more of the following parameters:
a flow of photons in the dose (mA), the patient size expressed as a water equivalent diameter ($D_W$), water equivalent diameter for a slice ($D_{W\_net}$), an estimation of radiation dose ($CTDI_{vol}$), a dose length product, the product of the $CTDI_{vol}$ and the length of the scan (DLP), SSDE, and noise;
transmit one or more of the parameters to the database; and
retrieve data from the DICOM header information, including one of: patient name, accession number, medical record number, date of birth, date of the examination, scanner, medical center, examination name.

54. The system of claim 22, further including the protocol manager being configured to perform the steps of:
receive an operator input to a range of acceptable image quality parameters;
receive the patient size as a water equivalent diameter $D_w$ and scanner parameters to calculate a SSDE for the range of acceptable image quality values;
recommend the SSDE that would generate images with acceptable image quality parameters;
allow an operator to manually set the SSDE; and
display an output on whether the expected image quality falls within the acceptable image quality parameters.

55. The system of claim 54, further including the protocol manager being configured to perform the steps of:
receive input for a target image quality parameter;
calculate a study with the input image quality parameter; and
recommend specific scan parameters, including at least one of: kV, mA, and dose modulation settings to achieve the input image quality.

56. The system of claim 54, further including the protocol manager being configured to perform the steps of:
provide an alert when SSDE is higher or lower than the recommended SSDE; and
provide an alert if the expected image quality falls outside the acceptable image quality parameters.

57. The system of claim 54, further including the protocol manager being configured to perform the step of:
display in a chart on a display operatively connected to the computerized system showing visually categorize which scans fell within expected image quality parameters versus which scans fell outside expected image quality parameters.

58. The system of claim 22, further including the protocol manager being configured to perform the steps of:
maintain one or more scan protocols for a plurality of scanners within a central database operatively connected to the system;
interface with a central protocol manager with a plurality of scanners to update protocol changes for the plurality of scanners.

59. The system of claim 22, further including the protocol manager being configured to perform the step of:
recommend a protocol to a patient of size based on previously acquired data.

* * * * *